United States Patent
Whipple et al.

(10) Patent No.: US 6,380,431 B1
(45) Date of Patent: Apr. 30, 2002

(54) FLUORESCENT MONOMERS

(75) Inventors: Wesley L. Whipple, Naperville; Patrick G. Murray, Yorkville, both of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/387,010

(22) Filed: Aug. 31, 1999

Related U.S. Application Data

(63) Continuation-in-part of application No. 08/843,407, filed on Apr. 15, 1997, now Pat. No. 5,986,030.

(51) Int. Cl.[7] .............................................. C07C 211/00
(52) U.S. Cl. ............................ 564/281; 560/8; 560/19; 526/268; 526/259; 526/260; 526/280
(58) Field of Search ............................... 564/281; 560/8, 560/19

(56) References Cited

U.S. PATENT DOCUMENTS

| | | | |
|---|---|---|---|
| 4,783,314 A | 11/1988 | Hoots et al. | 422/3 |
| 4,813,973 A | 3/1989 | Winnik et al. | 8/647 |
| 4,999,456 A | 3/1991 | Fong | 564/207 |
| 5,043,406 A | 8/1991 | Fong | 526/304 |
| 5,128,419 A | 7/1992 | Fong et al. | 525/351 |
| 5,171,450 A | 12/1992 | Hoots | 210/701 |
| 5,378,784 A | 1/1995 | Fong et al. | 526/307.5 |
| 5,408,022 A | 4/1995 | Imazato et al. | 526/259 |
| 5,435,969 A | 7/1995 | Hoots et al. | 422/14 |

FOREIGN PATENT DOCUMENTS

| | | | |
|---|---|---|---|
| JP | 1 141 147 | 1/1969 | C08F/19/00 |
| JP | 9-122472 | * 5/1997 | |

OTHER PUBLICATIONS

Sabirov et al. in Uzb. Khim. Zh. (1985), (2), 29–33.*
Sabirov et al. in Dokl. Akad. Nauk UzSSR (1983), (12), 26–28.*
Grinevich et al. in Polym. Prepr. (Am. Chem. Soc., Div. Polym. Chem.) (1998), 39(2), 683–684.*
The Use of Coumarin Derivatives in the Preparation of Fluorescence–Labeled Poly [N–(2–Hydroxypropyl)Methacrylamide], Collection Czechoslov, Chem Common, vol. 45, 1980, pp. 727–731.

* cited by examiner

*Primary Examiner*—Helen L. Pezzuto
(74) *Attorney, Agent, or Firm*—Margaret M. Brumm; Thomas M. Breininger

(57) ABSTRACT

Fluorescent monomers are described and claimed.

1 Claim, No Drawings

FLUORESCENT MONOMERS

CROSS-REFERENCE TO RELATED APPLICATIONS

This patent application is a continuation-in-part of U.S. patent application Ser. No. 08/843,407, filed Apr. 15, 1997, now U.S. Pat. No. 5,986,030.

FIELD OF THE INVENTION

This invention relates to the field of fluorescent moieties. Also described are water-soluble polymers incorporating fluorescent moieties. In addition, a method for determining the efficiency of polymers incorporating fluorescent moieties as water treatment agents is also disclosed.

BACKGROUND OF THE INVENTION

In many fields that employ polymers it may be desirable to tag or mark such polymers to facilitate monitoring thereof. By the term "monitoring" is meant herein any type of tracing or tracking to determine the location or route of the polymers, and any type of determination of the concentration or amount of the polymer at any given site, including singular or intermittent or continuous monitoring. For instance, it may be desirable to monitor Water treatment polymers in water systems, or to monitor polymers that may be present in waste fluids before disposal, or to monitor the polymer used for down-hole oil well applications, or to monitor polymers that may be present in fluids used to wash a manufactured product.

As seen from the above list of possible applications of polymer monitoring, the purpose of such monitoring may be to trace or track or determine the level of the polymer itself, or to trace or track or determine the level of some substance in association with the polymer, or to determine some property of the polymer or substance in association with the polymer, for instance its leachability.

Conventional techniques for monitoring polymers are generally time-consuming and labor intensive, and often require the use of bulky and/or costly equipment. Most conventional polymer analysis techniques require the preparation of calibration curves for each type of polymer employed, which is time-consuming and laborious, particularly when a large variety of polymer chemistries are being employed, and the originally prepared calibration curves lose their accuracy if the polymer structures change, for instance an acrylic acid ester mer unit being hydrolyzed to an acrylic acid mer unit.

Polymers tagged with pendant fluorescent groups are capable of being monitored, even when present at low concentrations. Some polymers tagged with pendant fluorescent groups are known. A process for preparing a polymer from the copolymerization of a fluorescent compound wherein an acrylamide moiety and the aromatic fluorescing moiety are directly linked through an amide bond to the aromatic ring is disclosed in Japanese Patent No. 1,141,147. Other fluorescent acrylamide based polymers are disclosed in U.S. Pat. Nos. 5,043,406 and 4,999,456. Polymers tagged with pendant fluorescent groups have been prepared by the transamidation derivatization of the pre-existing polymers having carbonyl-type pendant groups in U.S. Pat. No. 5,128,419. Another post-polymerization modification of a polyacrylamide with a fluorescing moiety is disclosed in U.S. Pat. No. 4,813,973. The preparation of certain vinylic coumarin derivatives is disclosed in *Collection Czechoslov. Chem Common*, Vol. 45, 1980, pgs. 727–731.

What are needed are additional fluorescent moieties that can be incorporated into tagged polymers which can be used in a variety of applications.

SUMMARY OF THE INVENTION

The first aspect of the invention are fluorescent monomers selected from the group consisting of:

MONOMER I

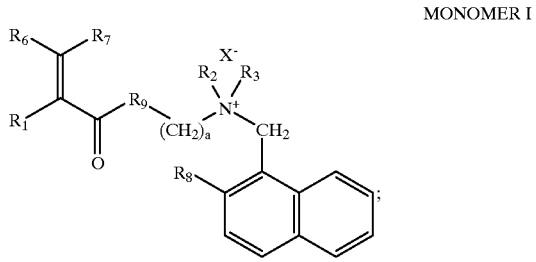

MONOMER II

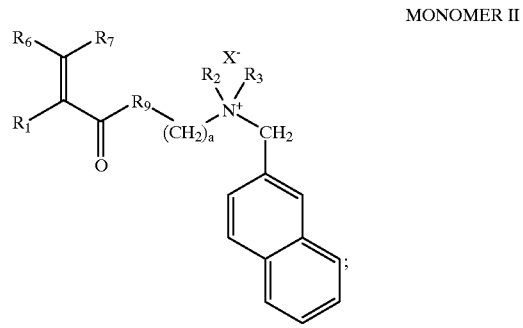

MONOMER III

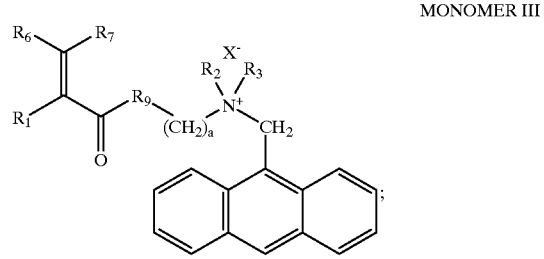

MONOMER IV

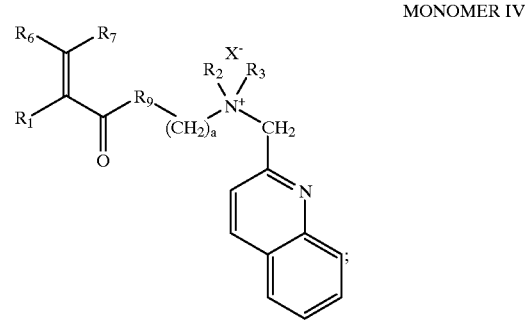

MONOMER V

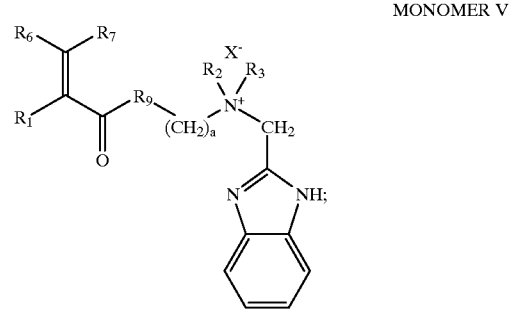

-continued
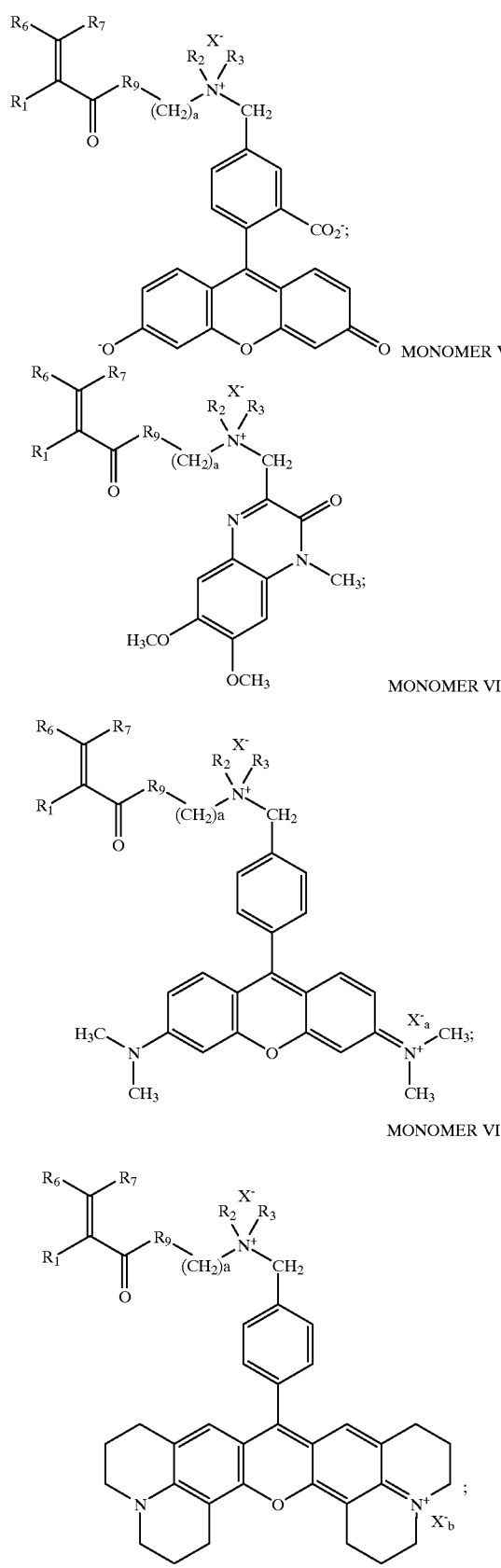
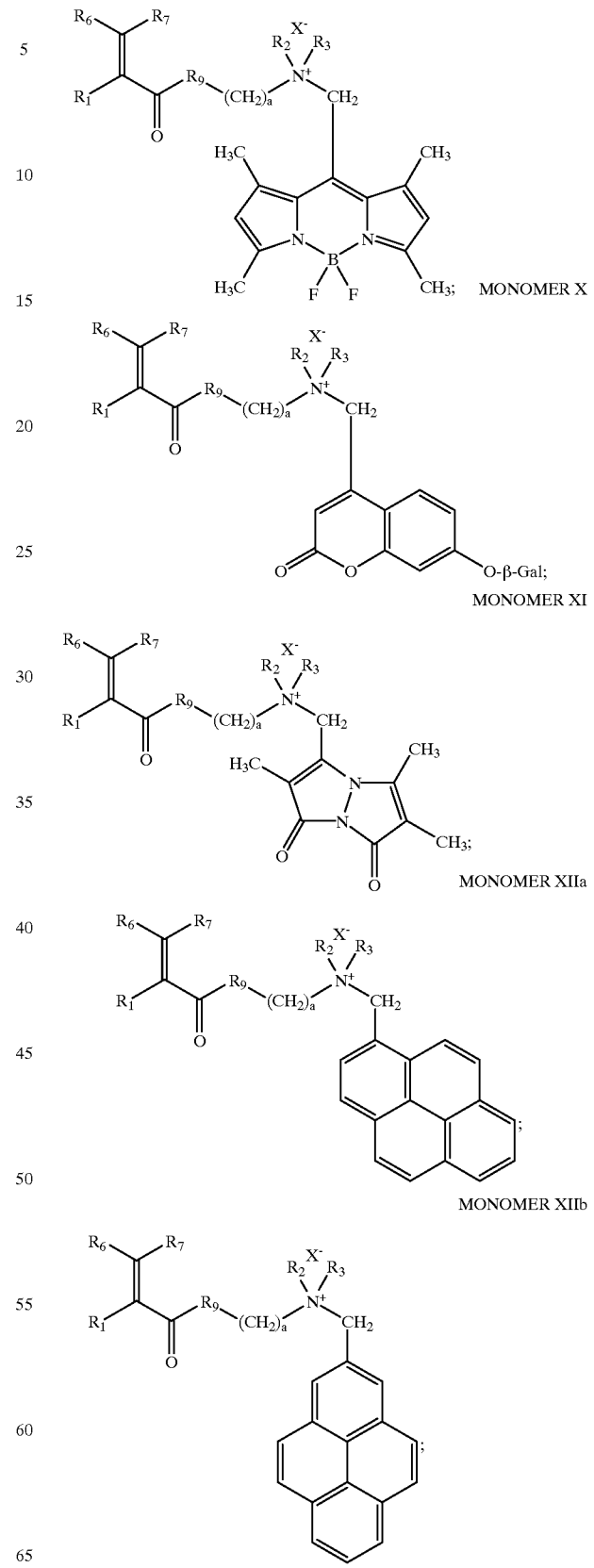

-continued

MONOMER XIIc

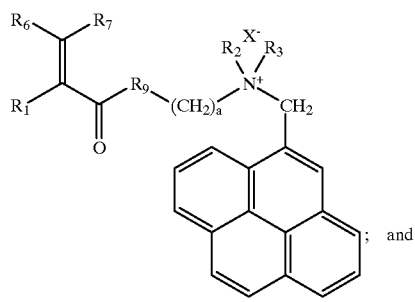

and

MONOMER XIII

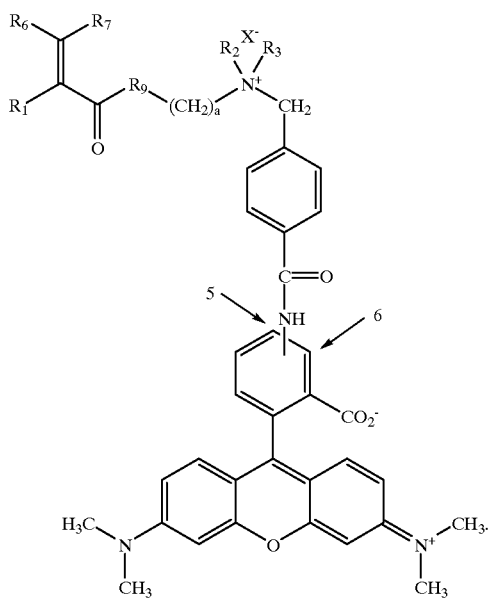

wherein a is an integer of from 1 to 10, $R_1$ is selected from the group consisting of hydrogen and methyl groups, $R_2$ and $R_3$ are methyl groups, $R_8$ is methyl, and $R_9$ is selected from the group consisting of NH and O;
where $R_6$ is either hydrogen or methyl; and
where $R_7$ is either hydrogen or methyl.

The second aspect of this invention is a water-soluble polymer of Formula Useful comprising from about 0.001 to about 10.0 mole percent of a Repeating Mer Unit represented by the formula:

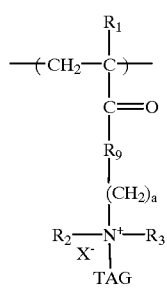

Repeating Mer Unit wherein a is an integer of from 1 to 10, $R_1$ is selected from the group consisting of hydrogen and methyl groups, $R_2$ and $R_3$ are methyl groups, and $R_9$ is selected from the group consisting of NH and O; TAG is a fluorescing moiety selected from the group consisting of:

TAG I

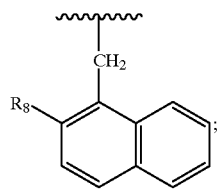

TAG II

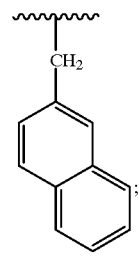

TAG III

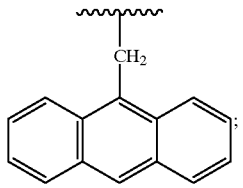

TAG IV

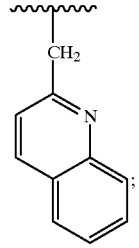

TAG V

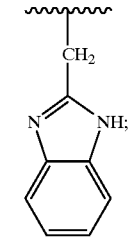

TAG VI

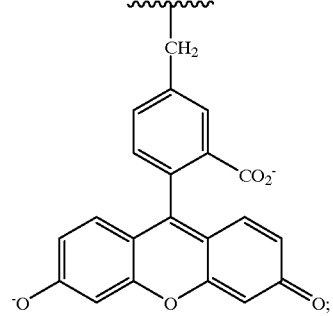

TAG VII, TAG VIIIa, TAG VIIIb, TAG IX, TAG X, TAG XI, TAG XIIa, TAG XIIb, TAG XIIc, TAG XIII and wherein the TAG is connected to the remainder of the mer unit thru the bond attached to the methylene group (—CH₂—) at the "top" of each TAG;
where $R_8$ is methyl;
O-β-Gal is β-D-galactopyranoside;
and X, $X^-_a$ and $X^-_b$ are selected from the group consisting of chloride, iodide, sulfate, acetate, benzoate, phosphate and bromide;
wherein the polymer of Formula Useful also comprises from about 90.0 to about 99.999 mole percent of one or more randomly distributed (one or more randomly distributed including block configurations) water-soluble vinylic mer units selected from one or more monomer groups consisting of acrylamide, methacrylamide, N,N-dimethylacrylamide, N,N-diethylacrylamide, acrylic acid, sodium acrylate, ammonium acrylate, methacrylic acid, sodium methacrylate, ammonium methacrylate, dimethylaminoethyl acrylate methyl chloride quaternary salt, dimethylaminoethyl acrylate benzyl chloride quaternary salt, dimethylaminoethyl acrylate methyl sulfate quaternary salt, dimethylaminoethyl methacrylate methyl sulfate quaternary salt, dimethylaminopropyl acrylamide methyl sulfate quaternary salt, dimethylaminopropyl methacrylamide methyl sulfate quaternary salt, diallyldimethylammonium chloride, N-vinylformamide, dimethylaminoethyl methacrylate acid salts, including, but not limited to, sulfuric acid salts and hydrochloric acid salts, dimethylaminoethyl methacrylate methyl chloride quaternary salt, dimethylaminoethyl methacrylate benzyl chloride quaternary salt, methacrylamidopropyltrimethylammonium chloride, acrylamidopropyltrimethylammonium chloride, N,N-methylenebisacrylamide, triallylamine, acid salts of triallylamine, ethylene glycol dimethacrylate, N-vinyl pyrrolidone, 2-acrylamido-2-methyl-1-propanesulfonic acid (AMPS), the sodium salt of AMPS, hydroxyethyl methacrylate, hydroxyethyl acrylate, hydroxypropyl acrylate, hydroxypropyl methacrylate, sodium vinyl sulfonate, styrene sulfonate, maleic acid, sodium salt of maleic acid, ammonium salt of maleic acid, N-isopropylacrylamide, diethylene glycol dimethacrylate, triethylene glycol, dimethylacrylate and polyethylene glycol dimethacrylate.

The third aspect of this invention is the use of polymers of Formula Useful as water soluble polymeric treating agents, wherein said polymer of Formula Useful comprises from about 0.001 to about 10.0 mole percent of a Repeating Mer Unit represented by the formula:

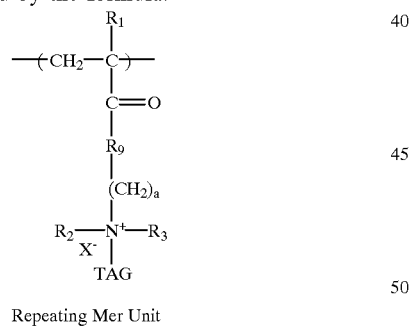

Repeating Mer Unit wherein a is an integer of from 1 to 10, $R_1$ is selected from the group consisting of hydrogen and methyl groups, $R_2$ and $R_3$ are methyl groups, and $R_9$ is selected from the group consisting of NH and O; TAG is a fluorescing moiety selected from the group consisting of:

TAG I

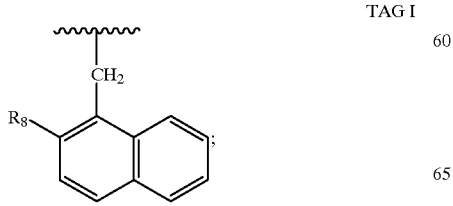

TAG II

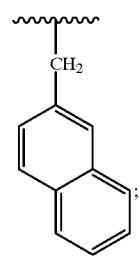

TAG III

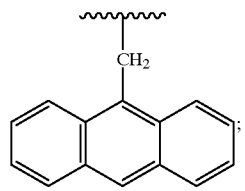

TAG IV

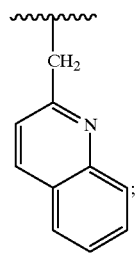

TAG V

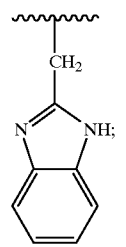

TAG VI

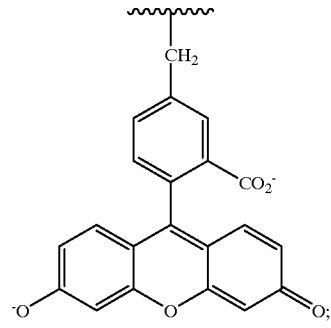

TAG VII

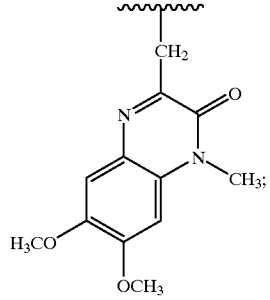

TAG VIIIa
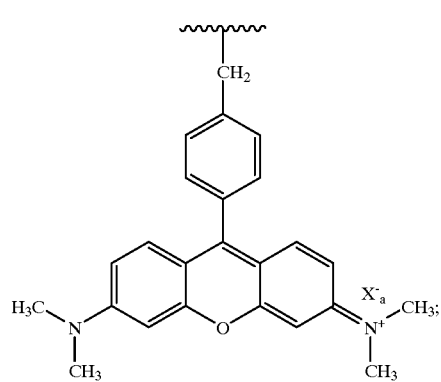
TAG VIIIb
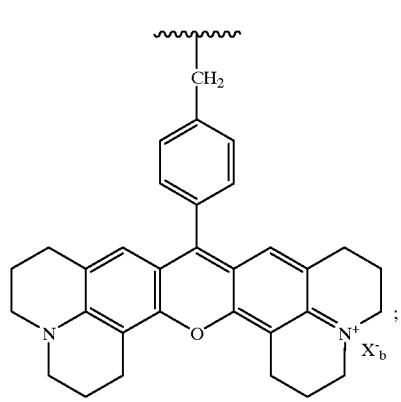
TAG IX
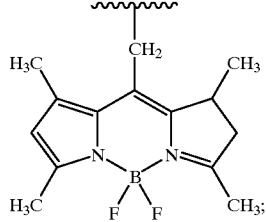
TAG X
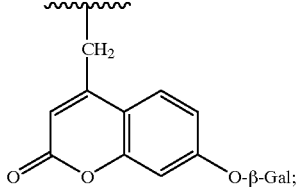
TAG XI
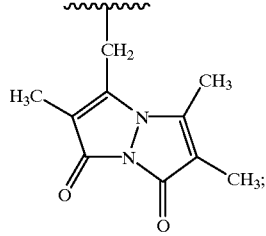
TAG XIIa
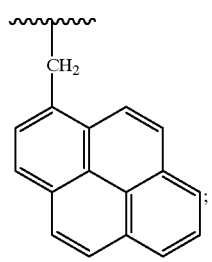
TAG XIIb
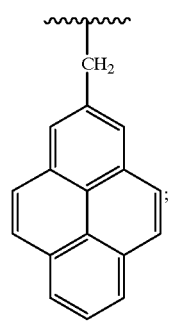
TAG XIIc
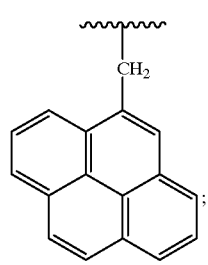
TAG XIII
and
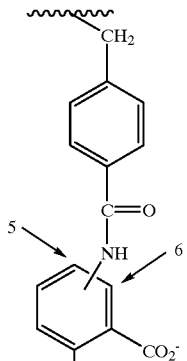
wherein the TAG is connected to the remainder of the mer unit thru the bond attached to the methylene group (—$CH_2$—) at the "top" of each TAG;
where $R_8$ is methyl;

O-β-Gal is β-D-galactopyranoside;

and X, $X^-_a$ and $X^-_b$ are selected from the group consisting of chloride, iodide, sulfate, acetate, benzoate, phosphate and bromide;

wherein the polymer of Formula Useful also comprises from about 90.0 to about 99.999 mole percent of one or more randomly distributed (one or more randomly distributed including block configurations) water-soluble vinylic mer units selected from one or more monomer groups consisting of acrylamide, methacrylamide, N,N-dimethylacrylamide, N,N-diethylacrylamide, acrylic acid, sodium acrylate, ammonium acrylate, methacrylic acid, sodium methacrylate, ammonium methacrylate, dimethylaminoethyl acrylate methyl chloride quaternary salt, dimethylaminoethyl acrylate benzyl chloride quaternary salt, dimethylaminoethyl acrylate methyl sulfate quaternary salt, dimethylaminoethyl methacrylate methyl sulfate quaternary salt, dimethylaminopropyl acrylamide methyl sulfate quaternary salt, dimethylaminopropyl methacrylamide methyl sulfate quaternary salt, diallyldimethylammonium chloride, N-vinylformamide, dimethylaminoethyl methacrylate acid salts, including, but not limited to, sulfuric acid salts and hydrochloric acid salts, dimethylaminoethyl methacrylate methyl chloride quaternary salt, dimethylaminoethyl methacrylate benzyl chloride quaternary salt, methacrylamidopropyltrimethylammonium chloride, acrylamidopropyltrimethylammonium chloride, N,N-methylenebisacrylamide, triallylamine, acid salts of triallylamine, ethylene glycol dimethacrylate, N-vinyl pyrrolidone, 2-acrylamido-2-methyl-1-propanesulfonic acid (AMPS), the sodium salt of AMPS, hydroxyethyl methacrylate, hydroxyethyl acrylate, hydroxypropyl acrylate, hydroxypropyl methacrylate, sodium vinyl sulfonate, styrene sulfonate, maleic acid, sodium salt of maleic acid, ammonium salt of maleic acid, N-isopropylacrylamide, diethylene glycol dimethacrylate, triethylene glycol, dimethylacrylate and polyethylene glycol dimethacrylate.

The fourth aspect of this invention is a method for maintaining the desired amount of water-soluble polymeric treating agents added to water comprising the steps of:

a) adding a water-soluble polymeric treating agent of Formula Useful to water such that a desired concentration of water-soluble polymeric treating agent of Formula Useful is present in said water, wherein said water-soluble polymeric treating agent of Formula Useful comprises from about 0.001 to about 10.0 mole percent of a Repeating Mer Unit represented by the formula:

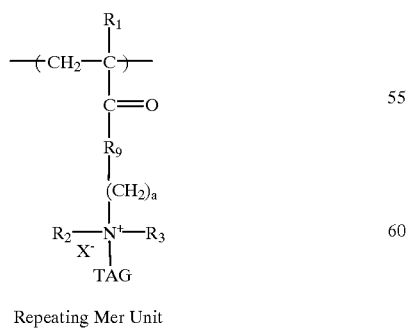

Repeating Mer Unit wherein a is an integer of from 1 to 10, $R_1$ is selected from the group consisting of hydrogen and methyl groups, $R_2$ and $R_3$ are methyl groups, and $R_9$ is selected from the group consisting of NH and O; TAG is a fluorescing moiety selected from the group consisting of:

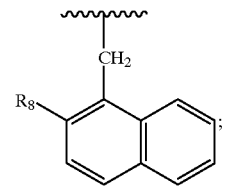

TAG I

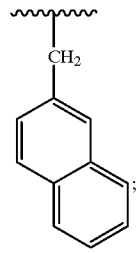

TAG II

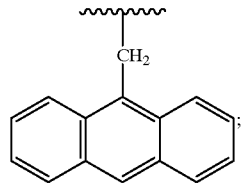

TAG III

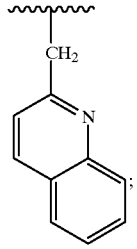

TAG IV

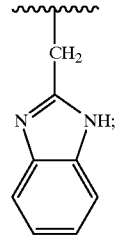

TAG V

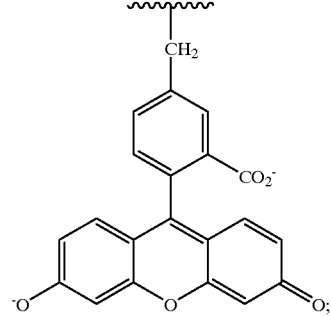

TAG VI wherein the TAG is connected to the remainder of the mer unit thru the bond attached to the methylene group (—CH₂—) at the "top" of each TAG;
where $R_8$ is methyl;
O-β-Gal is β-D-galactopyranoside;
and X, $X^-_a$ and $X^-_b$ are selected from the group consisting of chloride, iodide, sulfate, acetate, benzoate, phosphate and bromide;
wherein the polymer of Formula Useful also comprises from about 90.0 to about 99.999 mole percent of one or more randomly distributed (one or more randomly distributed including block configurations) water-soluble vinylic mer units selected from one or more monomer groups consisting of acrylamide, methacrylamide, N,N-dimethylacrylamide, N,N-diethylacrylamide, acrylic acid, sodium acrylate, ammonium acrylate, methacrylic acid, sodium methacrylate, ammonium methacrylate, dimethylaminoethyl acrylate methyl chloride quaternary salt, dimethylaminoethyl acrylate benzyl chloride quaternary salt, dimethylaminoethyl acrylate methyl sulfate quaternary salt, dimethylaminoethyl methacrylate methyl sulfate quaternary salt, dimethylaminopropyl acrylamide methyl sulfate quaternary salt, dimethylaminopropyl methacrylamide methyl sulfate quaternary salt, diallyldimethylammonium chloride, N-vinylformamide, dimethylaminoethyl methacrylate acid salts, including, but not limited to, sulfuric acid salts and hydrochloric acid salts, dimethylaminoethyl methacrylate methyl chloride quaternary salt, dimethylaminoethyl methacrylate benzyl chloride quaternary salt, methacrylamidopropyltrimethylammonium chloride, acrylamidopropyltrimethylammonium chloride, N,N-methylenebisacrylamide, triallylamine, acid salts of triallylamine, ethylene glycol dimethacrylate, N-vinyl pyrrolidone, 2-acrylamido-2-methyl-1-propanesulfonic acid (AMPS), the sodium salt of AMPS, hydroxyethyl methacrylate, hydroxyethyl acrylate, hydroxypropyl acrylate, hydroxypropyl methacrylate, sodium vinyl sulfonate, styrene sulfonate, maleic acid, sodium salt of maleic acid, ammonium salt of maleic acid, N-isopropylacrylamide, diethylene glycol dimethacrylate, triethylene glycol, dimethylacrylate and polyethylene glycol dimethacrylate;

b) analyzing the emissivity of said water as a measure of the concentration of said water-soluble polymeric treating agent of Formula Useful;

c) determining from the analysis of step b) that a change in concentration of said water-soluble polymeric treating agent of Formula Useful from the original concentration has occurred; and d) adjusting the concentration of said polymeric treating agent accordingly.

The fifth aspect of this invention is a method for determining the efficiency of water-soluble polymeric treating agents added to water comprising the steps of:

a) combining a predetermined amount of said water-soluble polymeric treating agent with a predetermined effective indicating amount of a water-soluble indicator polymer of Formula Useful, wherein said water-soluble indicator polymer of Formula Useful comprises from about 0.001 to about 10.0 mole percent of a Repeating Mer Unit represented by the formula:

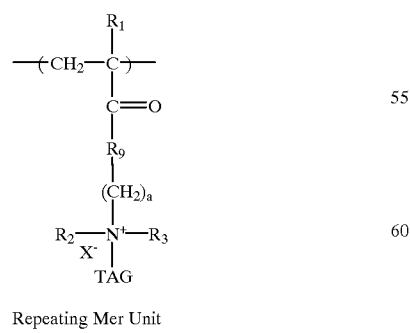

Repeating Mer Unit wherein a is an integer of from 1 to 10, $R_1$ is selected from the group consisting of hydrogen and methyl groups, $R_2$ and $R_3$ are methyl groups, and $R_9$ is selected from the group consisting of NH and O; TAG is a fluorescing moiety selected from the group consisting of:

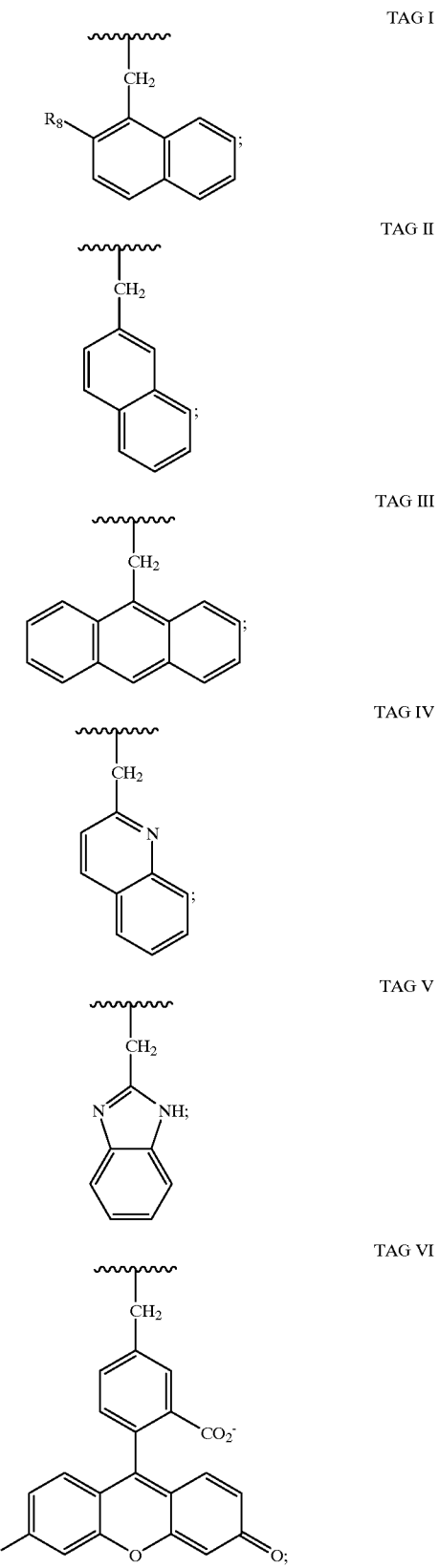

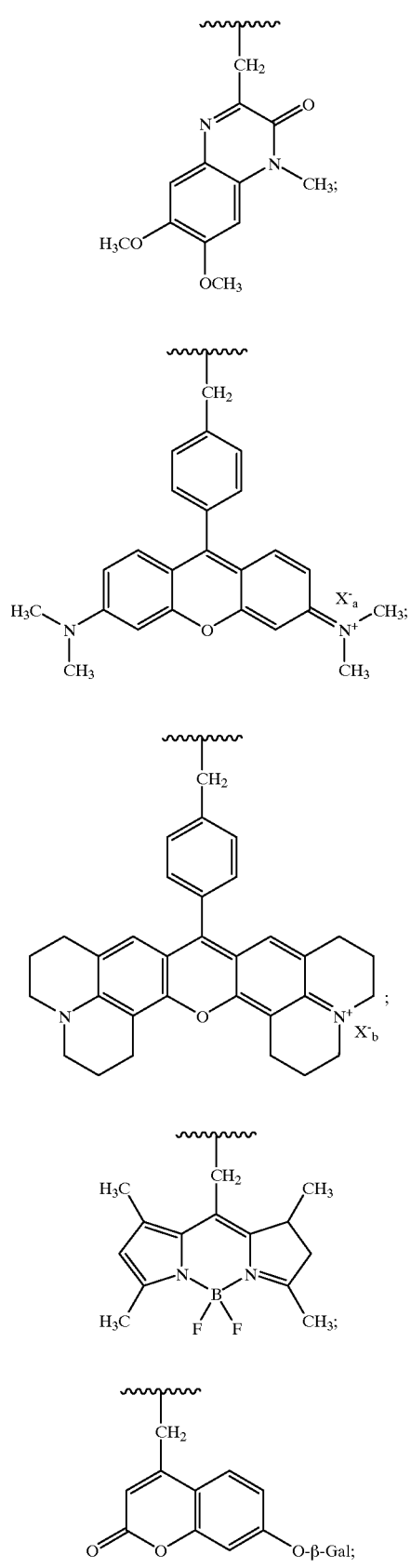
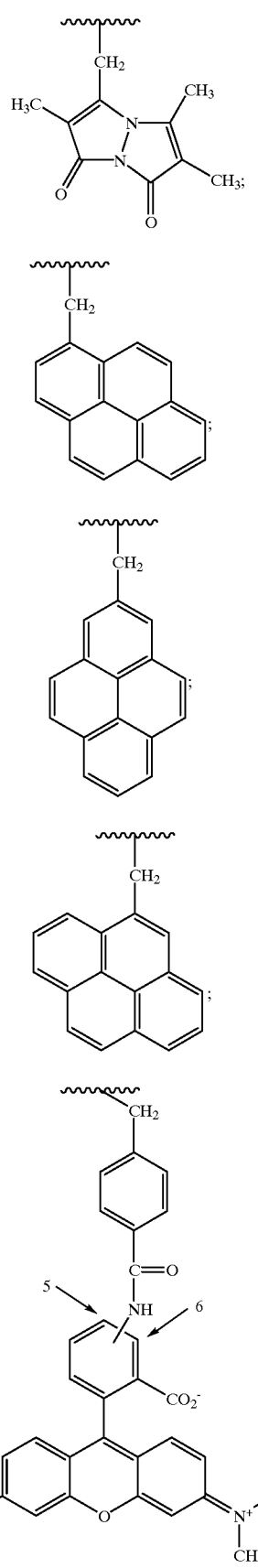

wherein the TAG is connected to the remainder of the mer unit thru the bond attached to the methylene group (—CH$_2$—) at the "top" of each TAG;

where R$_8$ is methyl;

O-β-Gal is β-D-galactopyranoside;

and X, X$^-_a$ and X$^-_b$ are selected from the group consisting of chloride, iodide, sulfate, acetate, benzoate, phosphate and bromide;

wherein the polymer of Formula Useful also comprises from about 90.0 to about 99.999 mole percent of one or more randomly distributed (one or more randomly distributed including block configurations) water-soluble vinylic mer units selected from one or more monomer groups consisting of acrylamide, methacrylamide, N,N-dimethylacrylamide, N,N-diethylacrylamide, acrylic acid, sodium acrylate, ammonium acrylate, methacrylic acid, sodium methacrylate, ammonium methacrylate, dimethylaminoethyl acrylate methyl chloride quaternary salt, dimethylaminoethyl acrylate benzyl chloride quaternary salt, dimethylaminoethyl acrylate methyl sulfate quaternary salt, dimethylaminoethyl methacrylate methyl sulfate quaternary salt, dimethylaminopropyl acrylamide methyl sulfate quaternary salt, dimethylaminopropyl methacrylamide methyl sulfate quaternary salt, diallyldimethylammonium chloride, N-vinylformamide, dimethylaminoethyl methacrylate acid salts, including, but not limited to, sulfuric acid salts and hydrochloric acid salts, dimethylaminoethyl methacrylate methyl chloride quaternary salt, dimethylaminoethyl methacrylate benzyl chloride quaternary salt, methacrylamidopropyltrimethylammonium chloride, acrylamidopropyltrimethylammonium chloride, N,N-methylenebisacrylamide, triallylamine, acid salts of triallylamine, ethylene glycol dimethacrylate, N-vinyl pyrrolidone, 2-acrylamido-2-methyl-1-propanesulfonic acid (AMPS), the sodium salt of AMPS, hydroxyethyl methacrylate, hydroxyethyl acrylate, hydroxypropyl acrylate, hydroxypropyl methacrylate, sodium vinyl sulfonate, styrene sulfonate, maleic acid, sodium salt of maleic acid, ammonium salt of maleic acid, N-isopropylacrylamide, diethylene glycol dimethacrylate, triethylene glycol, dimethylacrylate and polyethylene glycol dimethacrylate;

b) adding said water-soluble indicator polymer of Formula Useful and said water-soluble polymeric treating agent to said water;

c) analyzing the emissivity of said water as a measure of the concentration of said indicator polymer;

d) determining from the analysis of step c) that a change in concentration of said indicator polymer from said predetermined amount has occurred;

e) determining that a proportional change in said amount of said polymeric treating agent has occurred; and f) adjusting the concentration of said polymeric treating agent accordingly such that the desired concentration of said polymeric treating agent is present in said water.

DESCRIPTION OF THE INVENTION

Throughout this patent application, the following definitions will be used:

AcAm for acrylamide.

AIBN for 2,2'-azobis(isobutyronitrile)

AIR PRODUCTS is Air Products and Chemicals, Inc., 7201 Hamilton Boulevard, Allentown, Pa. 18195-1501, telephone number (610) 481-4911.

AIVN for 2,2'-azobis(2,4-dimethylvaleronitrile).

ALDRICH for Aldrich Chemical Company, P.O. Box 2060, Milwaukee, Wis., 53201, telephone numbers (414) 273-3850 or (800) 558-9160.

cP for centipoise.

Chain Transfer Agent is for any molecule, used in free-radical polymerization, which will react with a polymer radical forming a dead polymer and a new radical. Representative Chain Transfer Agents are listed by K. C. Berger and G. Brandrup, "Transfer Constants to Monomer, Polymer, Catalyst, Solvent, and Additive in Free Radical Polymerization," Section II, pp. 81–151, in "Polymer Handbook," edited by J. Brandrup and E. H. Immergut, 3d edition, 1989, John Wiley & Sons, New York.

Cross-Linking Agent for an ethylenically unsaturated monomer containing at least two sites of ethylenic unsaturation which is added to branch or increase the molecular weight of the water-soluble fluorescent polymer of this invention. Representative Cross-Linking Agents include N,N-methylenebisacrylamide, N,N-methylenebismethacrylamide, polyethylene glycol diacrylate, ethylene glycol dimethacrylate, diethylene glycol dimethacrylate, triethylene glycol dimethacrylate, polyethylene glycol dimethacrylate, polypropylene glycol dimethacrylate, N-vinyl acrylamide, divinyl benzene, triallyl ammonium salts, N-methyl allylacrylamide, glycidyl acrylate, acrolein, methylolacrylamide, glyoxal, epichlorohydrin, and the like. The cross linker is added at from about 0.0001 to about 10, preferably from about 0.0001 to about 0.2 weight percent based on the weight of the polymer.

Branching Agent for a Cross-Linking Agent that is administered at a low level (less than 0.05 weight percent based on the weight of the polymer). It is understood that Branching Agents are added to form "branches" not cross-links.

DADMAC for diallyldimethylammonium chloride.

DMAEA for dimethylaminoethyl acrylate.

DMAEM for dimethylaminoethyl methacrylate.

DMAEA·BCQ for dimethylaminoethyl acrylate, benzyl chloride quaternary salt.

DMAEA·MCQ for dimethylaminoethyl acrylate, methyl chloride quaternary salt.

DMAPMA for dimethylaminopropylmethacrylamide.

DMAPAA for dimethylaminopropylacrylamide

DMF for dimethylformamide.

DOW for The Dow Chemical Company, 2020 Dow Center, Midland Mich. 48686-0440, telephone numbers (517) 496-4000.

DUPONT for E.I. duPont de Nemours & Co. Inc., 1007 Market Street, Wilmington, Del. 19898, telephone numbers U.S. (800) 441-7515; worldwide (302) 774-1000.

EDTA·4Na$^+$ for ethylenediaminetetraacetic acid, tetrasodium salt.

EXXON for Exxon Chemical Co., 13501 Caty Freeway, Houston, Tex. 77079-1398, telephone number (281) 870-6712.

Halomethylfluorochrome for a fluorescent moiety which contains a —CH$_2$— halo component where halo is chloro, bromo or iodo. A halomethylfluorochrome can be used to form fluorescent quaternary (water soluble) monomers by reacting the halomethylfluorochrome with a tertiary amine containing monomer (DMAEA, DMAPMA, etc.).

HLB for hydrophilic-lipophilic balance number.

$^1$H-NMR for Proton Nuclear Magnetic Resonance Spectroscopy.

ICI for ICI Specialty Chemicals, Concord Plaza, 3411 Silverside Road, Wilmington, Del., telephone number (302) 887-3000.

KOHJIN for Kohjin Co., Ltd., 1-1, 1-Chome, Shimbashi, Minato-Ku, Tokyo, Japan, telephone number (03) 3504-3129.

MEHQ for the mono methyl ether of hydroquinone (4-methoxyphenol).

Mmol for millimole.

MOLECULAR PROBES for Molecular Probes, Inc., 4849 Pitchford Avenue, Eugene, Oreg. 97402-9165, telephone number (541) 465-8300.

NaCl for sodium chloride.

ROHM & HAAS is Rohm & Haas, 100 Independence Mall West, Philadelphia, Pa. 19106-2399, telephone number (215) 592-3000.

TLC for Thin-Layer Chromatography.

TRC for Toronto Research Chemicals, Inc., 2 Brisbane Rd., North York, ON M3J 2J8, telephone number 1-800-727-9240.

V-501 for 4,4'-azobis-(4-cyanopentanoic acid).

V-50 for 2,2'-azobis-(2-amidinopropane)dihydrochloride.

Versenex®80 for the pentasodium salt of diethylenetri-aminepentaacetic acid.

WAKO for Wako Chemicals USA, Inc., 1600 Bellwood Road, Richmond, Va. 23237, (804) 714-1920 or (800) 992-9256.

Indicator polymer, tagged polymer and fluorescent polymer are used interchangeably, and are meant to describe the polymers of the instant invention which are capable of fluorescing as a result of incorporation of a fluorescent moiety during polymerization.

RSV stands for Reduced Specific Viscosity. RSV is an indication of polymer chain length and average molecular weight. The RSV is measured at a given polymer concentration and temperature and calculated as follows:

$$RSV = \frac{[(\eta/\eta_0) - 1]}{c}$$

$\eta$ = viscosity of polymer solution
$\eta_0$ = viscosity of solvent at the same temperature
$c$ = concentration of polymer in solution.

In this patent application, the units of concentration "c" are (grams/100 ml or g/deciliter). Therefore, the units of RSV are dl/g. In this patent application, for measuring RSV, the solvent used was 1.0 molar sodium nitrate solution. The polymer concentration in this solvent was 0.045 g/dl. The RSV was measured at 30° C. unless otherwise indicated. The viscosities q and no were measured using a Cannon Ubbelohde semimicro dilution viscometer, size 75. The viscometer is mounted in a perfectly vertical position in a constant temperature bath adjusted to 30±0.02° C. The error inherent in the calculation of RSV is about 2 dl/grams. Within a series of polymer homologs, which are substantially linear, and well-solvated, polymers with similar RSV's have similar molecular weights according to Paul J. Flory, in "*Principles of Polymer Chemistry*", Cornell University Press, Ithaca, N.Y., © 1953, Chapter VII, "Determination of Molecular Weights"pp. 266–316.

IV stands for intrinsic viscosity, which is RSV extrapolated to the limit of infinite dilution, infinite dilution being when the concentration of polymer is equal to zero.

The monomers of the instant claimed invention are synthesized by following these procedures. Monomers I through III, VII, XIIa, XIIb, XIIc and XIII can be obtained by following this general procedure: A sample of a halomethyl fluorochrome is charged into a reaction flask along with acetone and a few crystals of MEHQ. The reaction mixture is heated to 56° C. To the resulting solution is added 3.3 molar equivalents of DMAPMA, DMAPAA, DMAEA, or DMAEM. The resulting mixture is refluxed until the vinylic quaternary salt (fluroescent vinylic monomer) is formed, typically in less than 2 hours. The progress of the reaction may be monitored by TLC. The reaction mixture is cooled, and the resulting precipitate is removed by filtration, washed with cold acetone and dried, yielding the fluorescent vinylic monomer as a solid.

Monomer IV can be obtained by following this general procedure: A mixture of 2-(chloromethyl)quinoline·HCl and a 1% sodium carbonate solution is added to a separatory funnel, and extracted with methylene chloride. The methylene chloride extracts are passed through a cone of anhydrous sodium sulfate, and collected in a flask. 2-(Chloromethyl) quinoline is obtained in the flask after evaporation of the methylene chloride. To the flask containing 2-(chloromethyl)quinoline, is added MEHQ and acetone. The mixture is heated to about 56° C. DMAPMA is added to the solution. The resulting mixture is heated for about 110 min at 56° C., then cooled to about 25° C. for 2 hrs. The resulting white solid, the quaternary ammonium salt of DMAPMA and 2-(chloromethyl)quinoline is isolated by filtration.

Monomer V and VI and VIIIa and VIIIb and IX and X and XI can be obtained by following this general procedure: A sample of the halomethyl flurorochrome, a few crystals of MEHQ and DMF is charged into a reaction flask. To the resulting solution is added about 3.3 equivalents of DMAPMA, DMAPAA, DMAEA or DMAEM. The resulting solution is heated to about 60° C. and maintained at that temperature until the quaternary monomer is formed. The progress of the reaction can be followed by using TLC. The resulting mixture is cooled, and used as a solution of the fluorescent vinylic monomer in DMF.

The monomers of the instant claimed invention can be used to make water-soluble polymers of Formula Useful comprising from about 0.001 to about 10 mole percent of a Repeating Mer Unit represented by the formula:

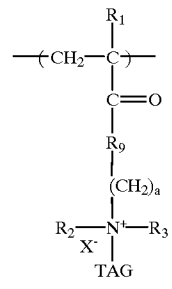

Repeating Mer Unit wherein a is an integer of from 1 to 10, $R_1$ is selected from the group consisting of hydrogen and methyl groups, $R_2$ and $R_3$ are methyl groups, $R_9$ is selected from the group consisting of NH and O; and TAG is a fluorescing moiety selected from the group consisting of: TAG I, TAG II, TAG III, TAG IV, TAG V, TAG VI, TAG VII, TAG VIIIa, TAG VIIIb, TAG IX, TAG X, TAG XI, TAG XIIa, TAG XIIb, TAG XIIc and TAG XIII; wherein the TAG is connected to the remainder of the mer unit thru the bond attached to the methylene group (—$CH_2$—) at the "top" of each TAG;

where $R_8$ is methyl;

O-β-Gal is β-D-galactopyranoside; and X, $X^-_a$ and $X^-_b$ are selected from the group consisting of chloride, iodide, sulfate, acetate, benzoate, phosphate and bromide ions;

wherein the polymer of Formula Useful also comprises from about 90.0 to about 99.999 mole percent of one or more randomly distributed (one or more randomly distributed including block configurations) water-soluble vinylic mer units selected from one or more of the monomer groups consisting of acrylamide, methacrylamide, N,N-dimethylacrylamide, N,N-diethylacrylamide, acrylic acid, sodium acrylate, ammonium acrylate, methacrylic acid, sodium methacrylate, ammonium methacrylate, dimethylaminoethyl acrylate methyl chloride quaternary salt, dimethylaminoethyl acrylate benzyl chloride quaternary salt, dimethylaminoethyl acrylate methyl sulfate quaternary salt, dimethylaminoethyl methacrylate methyl sulfate quaternary salt, dimethylaminopropyl acrylamide methyl sulfate quaternary salt, dimethylaminopropyl methacrylamide methyl sulfate quaternary salt, diallyldimethylammonium chloride, N-vinylformamide, dimethylaminoethyl methacrylate acid salts, including, but not limited to, sulfuric acid salts and hydrochloric acid salts, dimethylaminoethyl methacrylate methyl chloride quaternary salt, dimethylaminoethyl methacrylate benzyl chloride quaternary salt, methacrylamidopropyltrimethylammonium chloride, acrylamidopropyltrimethylammonium chloride, N,N-methylenebisacrylamide, triallylamine, acid salts of triallylamine, ethylene glycol dimethacrylate, N-vinyl pyrrolidone, 2-acrylamido-2-methyl-1-propanesulfonic acid (AMPS), the sodium salt of AMPS, hydroxyethyl methacrylate, hydroxyethyl acrylate, hydroxypropyl acrylate, hydroxypropyl methacrylate, sodium vinyl sulfonate, styrene sulfonate, maleic acid, sodium salt of maleic acid, ammonium salt of maleic acid, N-isopropylacrylamide, diethylene glycol dimethacrylate, triethylene glycol, dimethylacrylate and polyethylene glycol dimethacrylate.

Synthesis of Polymers

The first step in the synthesis of the polymers is to obtain the required monomer units.

Monomers I through XIII can be obtained as indicated previously.

Suitable vinylic mer units are selected from one or more of the monomer groups consisting of acrylamide, methacrylamide, acrylic acid, sodium acrylate, ammonium acrylate, methacrylic acid, sodium methacrylate, ammonium methacrylate, dimethylaminoethyl acrylate methyl chloride quaternary salt, dimethylaminoethyl acrylate benzyl chloride quaternary salt, dimethylaminoethyl acrylate methyl sulfate quaternary salt, dimethylaminoethyl methacrylate methyl sulfate quaternary salt, dimethylaminopropyl acrylamide methyl sulfate quaternary salt, dimethylaminopropyl methacrylamide methyl sulfate quaternary salt, diallyldimethylammonium chloride, N-vinylformamide, dimethylaminoethyl methacrylate acid salts, including, but not limited to, sulfuric acid salts and hydrochloric acid salts, dimethylaminoethyl methacrylate methyl chloride quaternary salt, dimethylaminoethyl methacrylate benzyl chloride quaternary salt, methacrylamidopropyltrimethylammonium chloride, acrylamidopropyltrimethyl ammonium chloride, N,N-methylenebisacrylamide, triallylamine, acid salts of triallylamine, ethylene glycol dimethacrylate, N-vinyl pyrrolidone, 2-acrylamido-2-methyl-1-propanesulfonic acid (AMPS), the sodium salt of AMPS, hydroxyethyl methacrylate, hydroxyethyl acrylate, hydroxypropyl acrylate, hydroxypropyl methacrylate, sodium vinyl sulfonate, styrene sulfonate, maleic acid, sodium salt of maleic acid, ammonium salt of maleic acid, N-isopropylacrylamide, diethylene glycol dimethacrylate, triethylene glycol, dimethylacrylate and polyethylene glycol dimethacrylate. These monomers can be synthesized using techniques known to a person of ordinary skill in the art of polymer synthesis or they can be purchased from ALDRICH or other sources. For example, hydroxyethylmethacrylate, hydroxyethylacrylate, hydroxypropylacrylate and hydroxypropyl methacrylate are available under the ROCRYL® trademark from ROHM & HAAS. Sodium vinyl sulfonate can be obtained from AIR PRODUCTS. N-isopropyl acrylamide is available from KOHJIN.

Polymers of Formula Useful contain at least two monomers: one monomer is selected from the group consisting of MONOMER I, MONOMER II, MONOMER III, MONOMER IV, MONOMER V, MONOMER VI, MONOMER VII, MONOMER VIIIa, MONOMER VIIIb, MONOMER IX, MONOMER X, MONOMER XI, MONOMER XIIa, MONOMER XIIb, MONOMER XIIc, and MONOMER XIII. The other monomer is selected from the group of suitable vinylic mer units previously listed. The mole percents of each monomer in polymers of Formula Useful have been previously given. In polymers of Formula Useful, it is possible to have one or more mer units selected from the group consisting of suitable vinylic mer units previously given. Preferred suitable vinylic mer units or combinations of suitable vinylic mer units include: DADMAC, acrylic acid, a combination of acrylamide and DMAEA·MCQ, and a combination of acrylamide and DADMAC.

After all of the requisite monomers have been obtained, polymers of Formula Useful can be synthesized, by following the procedure for making water-in-oil emulsion polymers or the procedure for making dispersion polymers or the procedure for making dry polymers or the procedure for making solution polymers.

The preparation of high molecular weight water-in-oil emulsion polymers has been described in the following references: U.S. Pat. No. 2,982,749 assigned to The Dow Chemical Company; U.S. Pat. No. 3,284,393 assigned to The Dow Chemical Company; U.S. Pat. No. 3,734,873 assigned to Nalco Chemical Company; "Mechanism, Kinetics and Modeling of the Inverse-Microsuspension Homopolymerization of Acrylamide," by D. Hunkeler, A. E. Hamielec, and W. Baade, W., *Polymer* (1989), 30(1), 127–42; and "Mechanism, Kinetics and Modeling of Inverse-Microsuspension Polymerization: 2. Copolymerization of Acrylamide with Quaternary Ammonium Cationic Monomers," by D. Hunkeler and A. E. Hamielec; *Polymer* (1991), 32(14), 2626–40.

A general procedure for the manufacture of water-in-oil emulsion polymers is provided to illustrate the preparation of these polymers using fluorescent monomers. The types and quantities of specific components in the formula (monomers, initiators, Chain Transfer Agents, for example) will vary depending upon the type of polymer (cationic, anionic, nonionic) that is being synthesized.

An aqueous phase is prepared by mixing together in water one or more water soluble monomers, and different polymerization additives such as inorganic salts, chelants, pH buffers, Chain Transfer Agents and Branching or Cross-Linking Agents. In order to synthesize the fluorescent water-soluble polymers of the instant claimed invention, a monomer selected from the group of Monomer I through Monomer XIII is included in the aqueous phase at the desired level.

An organic phase is prepared by mixing together an inert hydrocarbon liquid with one or more oil soluble surfactants. The surfactant mixture should have a low HLB, to ensure the formation of an oil continuous emulsion. Appropriate surfactants for water-in-oil emulsion polymerizations, which are commercially available, are compiled in the North American Edition of McCutcheon's *Emulsifiers & Detergents*. The oil phase may need to be heated to ensure the formation of a homogeneous oil solution.

The oil phase is charged into a reactor equipped with a mixer, a thermocouple, a nitrogen purge tube, and a condenser. Adding the aqueous phase to the reactor containing the oil phase with vigorous stirring forms an emulsion. The resulting emulsion is heated to the desired temperature, purged with nitrogen, and a free-radical initiator is added. The reaction mixture is stirred for several hours under a nitrogen atmosphere at the desired temperature. Upon completion of the reaction, the water-in-oil emulsion polymer is cooled to room temperature, where any desired post-polymerization additives, such as antioxidants, or a high HLB surfactant (as described in U.S. Pat. No. 3,734, 873) may be added.

The resulting emulsion polymer is a free-flowing liquid. An aqueous solution of the water-in-oil emulsion polymer can be generated by adding a desired amount of the emulsion polymer to water with vigorous mixing in the presence of a high-HLB surfactant (as described in U.S. Pat. No. 3,734, 873).

The preparation of dispersion polymers has been described in the following references: U.S. Pat. No. 4,929, 655, assigned to Hymo Corporation; U.S. Pat. No. 5,006, 590, assigned to Hymo Corporation; U.S. Pat. No. 5,597, 859, assigned to Nalco Chemical Company; European Patent 657,478; U.S. Pat. No. 5,597,858, assigned to Nalco Chemical Company and European Patent 630,909.

A general procedure for the manufacture of dispersion polymers is provided below in order to illustrate the preparation of dispersion polymers comprising the fluorescent monomers described herein. The types and quantities of specific components in the formula (salts and stabilizer polymers, for example) will vary depending upon the type of polymer (cationic, anionic, nonionic) that is being synthesized.

An aqueous solution containing one or more inorganic salts, one or more water-soluble monomers, any polymerization additives such as chelants, pH buffers, Chain Transfer Agents, Branching or Cross-Linking Agents and a water-soluble stabilizer polymer is charged to a reactor equipped with a mixer, a thermocouple, a nitrogen purging tube, and a water condenser. The monomer solution is mixed vigorously, heated to the desired temperature, and then a water-soluble initiator is added. The solution is purged with nitrogen whilst maintaining temperature and mixing for several hours. After this time, the products are cooled to room temperature, and any post-polymerization additives are charged to the reactor. Water continuous dispersions of water-soluble polymers are free flowing liquids with product viscosities generally 100–10,000 cP, measured at low shear. Thus, in order to prepare fluorescent water-soluble polymers as dispersions, a monomer selected from the group of Monomer I through Monomer XIII is included in the reaction mixture at the desired level.

A general procedure for the manufacture of dry powder polymers is provided below in order to illustrate the preparation of dry polymers comprising the fluorescent monomers described herein. The types and quantities of specific components in the formula (monomers, initiators, Chain Transfer Agents, for example) will vary depending upon the type of polymer (cationic, anionic, nonionic) that is being synthesized.

An aqueous solution of water-soluble monomers, generally 20–60 percent concentration by weight, along with any polymerization or process additives such as Chain Transfer Agents, Branching or Cross-Linking Agents, chelants, pH buffers, or surfactants, is warmed to an appropriate temperature and placed in an insulated reaction vessel equipped with a nitrogen purging tube. A polymerization initiator is added, the solution is purged with nitrogen, and the temperature of the reaction is allowed to rise uncontrolled. When the polymerized mass is cooled, the resultant gel is removed from the reactor, shredded, dried, and ground to the desired particle size. Thus, in order to prepare fluorescent water-soluble polymers as dry powders, a monomer selected from the group of Monomer I through Monomer XIII is included in the reaction mixture at the desired level.

A general procedure for the manufacture of solution polymers is provided to illustrate the preparation of these polymers using fluorescent monomers. The types and quantities of specific components in the formula (monomers, initiators, Chain Transfer Agents, for example) will vary depending upon the type of polymer (cationic, anionic, nonionic) that is being synthesized:

An aqueous solution containing one or more water soluble monomers and any polymerization additives such as chelants, pH buffers, Chain Transfer Agents, Branching Agents or Cross Linking Agents is prepared. This mixture is charged to a reactor equipped with a mixer, a thermocouple, a nitrogen purging tube and a water condenser. The solution is mixed vigorously, heated to the desired temperature, and then one or more water soluble free radical polymerization initiators are added. The solution is purged with nitrogen whilst maintaining temperature and mixing for several hours. Typically, the viscosity of the solution increases during this period. After the polymerization is complete, the reactor contents are cooled to room temperature and then transferred to storage. Solution polymer viscosities vary widely, and are dependent upon the concentration and molecular weight of the active polymer component. Thus, in order to prepare fluorescent water soluble solution polymers, a monomer selected from the group of Monomer I through Monomer XIII is included in the reaction mixture at the desired level.

Once synthesized, the polymers of Formula Useful are useful as water soluble polymeric treatment agents.

One such utility for the polymers of Formula Useful is their use in the dewatering of sludge. The typical amount of polymer used in dewatering of sludge is from about 3 ppm to about 1000 ppm, preferably from about 10 ppm to about 400 ppm and most preferably from about 20 ppm to about 200 ppm.

Another utility for the polymers of Formula Useful is their use as retention and drainage aids. The polymer functions as a flocculant during the papermaking process with the flocculant added to enhance the retention and drainage properties of the pulp/paper. Retention and drainage are important properties of a papermaking process that papermakers are always seeking to optimize. Details concerning the art of making paper and the necessity for having acceptable retention and drainage properties of the pulp/paper during processing can be found in any standard reference text in the art of papermaking. Once such text, is "PAPER BASICS: Forestry, Manufacture, Selection, Purchasing, Mathematics and Metrics, Recycling" by David Saltman, © 1978 by Van Norstrand Reinhold Company, published by Krieger Publishing Company, Krieger Drive, Malabar, Fla. 32950.

The typical amount of polymer used for a retention and drainage aid in pulp and paper applications is from about 0.25 lbs active/ton of solids in furnish to about 6.0 lbs active/ton of solids. More preferably, the amount of polymer added is from about 0.5 lbs active/ton of solid in furnish to about 4 lbs active/ton of solids in furnish and most preferably, the amount of the polymer added is about 2 lbs actives/ton of solids in furnish. The dose of polymer recited herein is based on pounds of actual polymer, not pounds of liquid that contains polymer.

The polymers of Formula Useful can be used in a method for maintaining the desired amount of water-soluble polymeric treating agent of Formula Useful added to water comprising the steps of:

a) adding a water-soluble polymeric treating agent of Formula Useful to water such that a desired concentration of water-soluble polymeric treating agent of Formula Useful is present in said water;
b) analyzing the emissivity of said water as a measure of the concentration of said water-soluble polymeric treating agent of Formula Useful;
c) determining from the analysis of step b) that a change in concentration of said water-soluble polymeric treating agent of Formula Useful from the original concentration has occurred; and
d) adjusting the concentration of said polymeric treating agent accordingly.

The waters may be either natural or industrial waters. Natural waters are also referred to as "untreated" or "raw" waters. The industrial waters may be municipal wastewaters, chemical processing wastewaters, boiler water, cooler water, water utilized in papermaking and mining applications and water used in any other industrial application which requires treatment.

The "desired concentration of water-soluble polymeric treating agent of Formula Useful" is known or readily determinable by experiments that are known to one of ordinary skill in the art. It is also known that the concentration of water-soluble-polymeric treating agent of Formula Useful can be indirectly measured by measuring the emissivity of the water sample. The standard technique of relating emissivity to concentration is by the use of a calibration curve for each polymer that plots emissivity against the known concentration of polymer in the sample. A person of ordinary skill in the art also would know how to create these calibration curves.

As utilized herein, the term "analyzing the emissivity" refers to monitoring by a fluorescence technique. Such techniques, and required calculations to correlate fluorescence to concentration are described in U.S. Pat. Nos. 4,783,314; 4,992,380; 5,171,450; and 5,435,969; which are hereby incorporated by reference.

By the term "adjusting the concentration of said polymeric treating agent accordingly" is meant that the amount of the water-soluble polymeric treating agent of Formula Useful being added to said water is adjusted based on some significant change in the fluorescence measurement. The actual fluorescence measurement may either increase or decrease depending on the application, as a function of polymer dosage, or the relative changes in the fluorescence measurement may either become larger or smaller as a function of polymer dosage. When such changes occur at or near the optimum polymer dosage as represented by some other parameter of interest (for example drainage, retention, sludge dewatering, etc.) then the trends in the fluorescence measurement can be used to determine and maintain the proper dosage of the polymeric treating agent for the particular parameter of interest. The method is particularly suited to applications where such instantaneous feedback could be provided by an in-line fluorescence monitoring device which would be used as part of a system to control a polymer feeding pump, for example, wherein the polymer dosage is increased or decreased depending on the response from the fluorescence measurement device.

For instance, it may be, desirable to monitor water treatment polymers in water systems, particularly industrial water systems, or to monitor polymers that may be present in waste fluids before disposal, particularly industrial waste fluids, or to, monitor the polymer used for down-hole oil well applications, particularly the route taken after introduction down-hole, or to monitor polymers that may ,be present in fluids used to wash a manufactured product, for instance a polymer-coated product, to determine the amount of polymer washed or leached therefrom. By fluids or liquids as used herein generally is meant aqueous, non-aqueous, and mixed aqueous/non-aqueous fluid systems. In addition, the polymers of Formula Useful can be used in a method for determining the efficiency of water-soluble polymeric treating agents added to water comprising the steps of:

a) combining a predetermined amount of said water-soluble polymeric treating agent with a predetermined effective indicating amount of a water-soluble indicator polymer of Formula Useful;
b) adding said water-soluble indicator polymer of Formula Useful and said water-soluble polymeric treating agent to said water;
c) analyzing the emissivity of said water as a measure of the concentration of said indicator-polymer;
d) determining from the analysis of step c) that a change in concentration of said indicator polymer from said predetermined amount has occurred;
e) determining that a proportional change in said amount of said polymeric treating agent has occurred; and
f) adjusting the concentration of said polymeric treating agent accordingly such that the desired concentration of said polymeric treating agent is present in said water.

As used herein, the term water-soluble polymeric treating agent refers to polymers which are added to aqueous systems for the purpose of scale control, corrosion inhibition, dispersing polymers, flocculating polymers, coagulating polymers and thickening polymers among others. The term predetermined amount, in reference to the water-soluble polymeric treating agent, refers to an amount known to a person of normal skill in the art as being required by the system to effect a particular treatment. For example, if the water is a boiler water, the predetermined amount would be the effective scale-preventing amount of polymer required by that particular aqueous system to prevent scale. As used herein, the term predetermined effective indicating amount refers to a minimal amount that can be detected by a fluorescence technique (above the native fluorescence of the aqueous system being treated).

The water-soluble polymeric treating agent and the water-soluble polymeric indicator of Formula Useful may be blended prior to addition, or added individually in sequential fashion. Once they have been added to the system, the water can be analyzed fluorometrically to look for the indicator polymer. The amount of indicator polymer found is then used to calculate the amount of water-soluble polymeric treating agent present. The amount of water-soluble polymeric treating agent being added to the water is then adjusted either upwards or downwards in order to provide for the desired concentration of water-soluble polymeric treating agent in the water.

EXAMPLES

The following examples are intended to be illustrative of the present invention and to teach one of ordinary skill how to make and use the invention. These examples are not intended to limit the invention or its protection in any way.

Monomer Example Ia

Monomer Ia, is Monomer I when $R_1$ and $R_2$ and $R_3$ are all methyl ($CH_3$), $R_6$ and $R_7$ and $R_8$ are all H, $R_9$ is NH, a is 3 and X is Cl. Monomer Ia is a quaternary ammonium salt of DMAPMA and 1-(chloromethyl)naphthalene. Monomer Ia can be synthesized by following this procedure:

To a 50 ml pear-shaped flask, equipped with a magnetic stir bar, Claisen tube, and condenser, is added 14.1 mg (0.08 mmol) of 1-(chloromethyl)naphthalene (available from ALDRICH), 0.4 mg of MEHQ, and 3.2 ml of acetone. A solution results when the mixture is heated to 56° C. DMAPMA (44.2 mg, 0.26 mmol) is added by syringe to the solution. The resulting mixture is heated for 110 min at 56° C. At 54 minutes, a white solid is observed in the flask. The reaction mixture is allowed to stand at room temperature for 120 min. The white solid is isolated by filtration through a sintered glass funnel, then washed with 3–2 ml portions of acetone. The quaternary ammonium salt of DMAPMA and 1-(chloromethyl)naphthalene is obtained as a solid.

Monomer Example Ib

Monomer Ib, is Monomer I when $R_1$ and $R_2$ and $R_3$ and $R_8$ are all methyl ($CH_3$), $R_6$ and $R_7$ are both H, $R_9$ is NH, a is 3 and X is Cl. Monomer Ib is a quaternary ammonium salt of DMAPMA and 1-chloromethyl-2-methylnaphthalene. Monomer Ib is synthesized using the same procedure as for Monomer I when $R_8$ is H and X is Cl, except substituting 15.3 mg (0.08 mmol) of 1-chloromethyl-2-methylnaphthalene (available from ALDRICH) for 1-(chloromethyl)naphthalene. The quaternary ammonium salt of DMAPMA and 1-chloromethyl-2-methylnaphthalene is obtained as a solid.

Monomer Example II

Monomer II; when $R_1$ and $R_2$ and $R_3$ are all methyl ($CH_3$), $R_6$ and $R_7$ are both H, $R_9$ is NH, a is 3 and X is Br; is a quaternary ammonium salt of DMAPMA and 2-(bromomethyl)naphthalene which is obtained using the same procedure as for Monomer Ia, except substituting 17.7 mg (0.08 mmol) of 2-(bromomethyl)naphthalene (available from ALDRICH) for 1-(chloromethyl)naphthalene. Monomer II is obtained as a solid.

Monomer Example III

Monomer III, when $R_1$ and $R_2$ and $R_3$ are all methyl ($CH_3$), $R_6$ and $R_7$ are both H, $R_9$ is NH, a is 3 and X is Cl; is a quaternary ammonium salt of DMAPMA and 9-(chloromethyl)anthracene, which is synthesized using the same procedure as for Monomer Ia, except substituting 18.1 mg (0.08 mmol) of 9-(chloromethyl)anthracene (available from ALDRICH) for 1-(chloromethyl)naphthalene. Monomer III is obtained as a solid.

Monomer Example IV

Monomer IV, when $R_1$ and $R_2$ and $R_3$ are all methyl ($CH_3$), $R_6$ and $R_7$ are both H, $R_9$ is NH, a is 3 and X is Cl; is a quaternary ammonium salt of DMAPMA and 2-(chloromethyl)quinoline, which is synthesized in the following manner. A mixture of 2-(chloromethyl)quinoline·HCl (171 mg, 0.8 mmol; available from ALDRICH) and 7 ml of a 1% sodium carbonate solution is added to a separatory funnel, and extracted with two, 7 ml portions of methylene chloride. The methylene chloride extracts are passed through a cone of anhydrous sodium sulfate, and collected in a 50 ml flask. 2-(Chloromethyl)quinoline is obtained in the flask after evaporation of the methylene chloride. To the 50 ml flask containing 2-(chloromethyl)quinoline, is added 4 mg of MEHQ and 32 ml of acetone. The flask is equipped with a magnetic stir bar, Claisen tube, and condenser. The mixture is heated to 56° C. DMAPMA (0.44 g, 2.6 mmol) is added by syringe to the solution. The resulting mixture is heated for 110 min at 56° C., then cooled to room temperature for 2 hrs. The resulting white solid, the quaternary ammonium salt of DMAPMA and 2-(chloromethyl)quinoline is isolated by filtration as described for Monomer Ia.

Monomer Example V

Monomer V, when $R_1$ and $R_2$ and $R_3$ are all methyl ($CH_3$), $R_6$ and $R_7$ are both H, $R_9$ is NH, a is 3 and X is Cl; is a quaternary ammonium salt of DMAPMA and 2-(chloromethyl)benzimidazole which is synthesized by following this procedure: To a 25 -ml pear-shaped flask, equipped with a magnetic stir bar, Claisen tube, and condenser is added 2-(chloromethyl)benzimidazole (4.7 mg, 0.028 mmol), 1 small crystal of MEHQ, and 1.00 g of DMF. A solution results upon stirring. DMAPMA (14.5 mg, 0.0845 mmol) is added to the solution. The resulting mixture is heated for 135 min. The quaternary salt does not have to be isolated, rather, it is used as a solution in dimethylformamide (concentration approximately 0.96 weight %).

Monomer Example VI

Monomer VI, when $R_1$ and $R_2$ and $R_3$ are all methyl ($CH_3$), $R_6$ and $R_7$ are both H, $R_9$ is NH, a is 3 and X is Br; is a quaternary ammonium salt of DMAPMA and 5-(bromomethyl)fluorescein. Monomer VI is synthesized using the same procedure as Monomer V, except substituting 5-(bromomethyl)fluorescein for 2-(chloromethyl)benzimidazole. A solution of Monomer VI in DMF of about 1.68 weight % is obtained.

TLC can be used to monitor the progress of the reaction.

Monomer Example VII

Monomer VII, when $R_1$ and $R_2$ and $R_3$ are all methyl ($CH_3$), $R_6$ and $R_7$ are both H, $R_9$ is NH, a is 3 and X is Br; is a quaternary ammonium salt of DMAPMA and 3-(bromomethyl)-6,7-dimethoxy-1-methyl-2(1H)-quinoxazolinone. Monomer VII is synthesized in the same way as Monomer Ia, except substituting 3-(bromomethyl)-6,7-dimethoxy-1-methyl-2(1H)-quinoxazolinone (available from MOLECULAR PROBES) 25 mg, 0.080, for 1-(chloromethyl)naphthalene.

By following this procedure, the DMAPMA-3-(bromomethyl)-6,7-dimethoxy-1-methyl-2(1H)-quinoxazolinone quaternary salt, is obtained in 88% yield (34 mg) as a white solid. The structure is confirmed by $^1$H-NMR.

NMR Data for Monomer VII (quaternary salt of DMAPMA and the Quinoxazolinone); $^1$H NMR ($D_2O$, 400 MHz) δ 1.63 (s, 3H), 2.08 (br s, 2H), 3.27 (s, 6H), 3.30 (br s, 2H), 3.50 (m, 2H), 3.72 (s, 3H), 3.92 (s, 3H), 4.01 (s, 3H), 4.65 (m, 2H), 5.23 (s, 1H), 5.45 (s, 1H), 6.99 (s, 1H), 7.38 (s, 1H).

Monomer Example VIIIa

A solution of Monomer VIIIa, is a solution of Monomer VIII, when $R_1$ and $R_2$ and $R_3$ are all methyl ($CH_3$), $R_6$ and $R_7$ are both H, $R_9$ is NH, a is 3 and X is Cl. A solution of Monomer VIIIa is a quaternary ammonium salt of DMAPMA and 9-(4-(chloromethyl)phenyl)-3,6-bis(dimethylamino)xanthylium chloride, in DMF. A solution of Monomer VIIIa is synthesized using the same procedure as for Monomer V; except substituting 12.0 mg (0.028 mmol) of 9-[4-(chloromethyl)phenyl]-3,6-bis(dimethylamino)xanthylium chloride (MitoTracker™ Orange CMTMRos, available from MOLECULAR PROBES) for 2-(chloromethyl)benzimidazole. A 1.70 weight % solution of Monomer VIIIa in DMF is obtained.

Monomer Example VIIIb

A solution of Monomer VIIIb; is a solution of Monomer VIII, when $R_1$ and $R_2$ and $R_3$ are all methyl ($CH_3$), $R_6$ and $R_7$ are both H, $R_9$ is NH, a is 3 and X is Cl. A solution of Monomer VIIIb is a quaternary ammonium salt of DMAPMA and 9-(4-(chloromethyl)phenyl)-2,3,6,7,12,13,16,17-octahydro-1H,5H,11H,15H-xantheno(2,3,4-ij:5,6,7-i'j')diquinolizin-18-ium chloride, in DMF. A solution of Monomer VIIIb is synthesized using the same procedure as for Monomer V, except substituting 15.0 mg (0.028 mmol) of 9-(4-(chloromethyl)phenyl)-2,3,6,7,12,13,16,17-octahydro-1H,5H,11H,15H-xantheno(2,3,4-ij:5,6,7-i'j') diquinolizin-18-ium chloride (MitoTracker™ Red, CMXRos, available from MOLECULAR PROBES) for 2-(chloromethyl)benzimidazole. A 1.99 weight % solution of Monomer VIIIb in DMF is obtained.

Monomer Example IXa

A solution of Monomer IXa, is a solution of Monomer IX, when $R_1$ and $R_2$ and $R_3$ are all methyl ($CH_3$), $R_6$ and $R_7$ are both H, $R_9$ is NH, a is 3 and X is Cl. A solution of Monomer IXa is a quaternary ammonium salt of DMAPMA and 8-chloromethyl-4,4-difluoro-1,3,5,7-tetramethyl-4-bora-3a,4a-diaza-s-indacene (CellTracker™ Green BODIPY®), in DMF. A solution of Monomer IXa is synthesized using the same procedure as for Monomer V, except substituting 8.3 mg (0.028 mmol) of 8-chloromethyl-4,4-difluoro-1,3,5,7-tetramethyl-4-bora-3a,4a-diaza-s-indacene (CellTracker™ Green BODIPY®), available from MOLECULAR PROBES) for 2-(chloromethyl)benzimidazole. A 1.32 weight % solution of Monomer IXa, is obtained.

Monomer Example IXb

A solution of Monomer IXb, is a solution of Monomer IX when $R_1$ and $R_2$ and $R_3$ are all methyl ($CH_3$), $R_6$ and $R_7$ are both H, $R_9$ is NH, a is 3 and X is Br. A solution of Monomer IXb is a quaternary ammonium salt of DMAPMA and 8-bromomethyl-4,4-difluoro-1,3,5,7-tetramethyl-4-bora-3a,4a-diaza-s-indacene (BODIPY 493/503 methyl bromide) in DMF. A solution of Monomer IXb is synthesized using the same procedure as for Monomer V, except substituting 9.6 mg (0.028 mmol) of 8-bromomethyl-4,4-difluoro-1,3,5,7-tetramethyl-4-bora-3a,4a-diaza-s-indacene (BODIPY 493/503 methyl bromide, available from MOLECULAR PROBES) for 2-(chloromethyl)benzimidazole. A 1.45 weight % solution of Monomer IXb in DMF is obtained.

Monomer Example X

A solution of Monomer X, when $R_1$ and $R_2$ and $R_3$ are all methyl ($CH_3$), $R_6$ and $R_7$ are both H, $R_9$ is NH, a is 3 and where X is Cl; is a quaternary ammonium salt of DMAPMA and 4-chloromethylcoumarin-7yl-β-D-galactopyranoside (DetecTAGene™ Blue CMCG), in DMF, which is synthesized using the same procedure as for Monomer V, except substituting 10.4 mg (0.028 mmol, actives) of 4-chloromethylcoumarin-7yl-β-D-galactopyranoside (DetecTAGene™ Blue CMCG (aqueous DMSO solution) available from MOLECULAR PROBES) for 2-(chloromethyl)benzimidazole. A 1.54 weight % solution of Monomer X in DMF is obtained.

Monomer Example XI

A solution of Monomer XI, when $R_1$ and $R_2$ and $R_3$ are all methyl ($CH_3$), $R_6$ and $R_7$ are both H, $R_9$ is NH, a is 3 and where X is Br, is a quaternary ammonium salt of DMAPMA and monobromobimane, in DMF. A solution of Monomer XI is synthesized using the same procedure as for Monomer V, except substituting 7.6 mg (0.028 mmol) of monobromobimane (available from MOLECULAR PROBES) for 2-(chloromethyl)benzimidazole. A 1.25 weight % solution of Monomer XI in DMF is obtained.

Monomer Example XIIa

Monomer XIIa, when $R_1$ and $R_2$ and $R_3$ are all methyl ($CH_3$), $R_6$ and $R_7$ are both H, $R_9$ is NH, a is 3 and X is Br; is a quaternary ammonium salt of DMAPMA and 1-(bromomethyl)pyrene. Monomer XIIa is synthesized using the same procedure as for Monomer I, except substituting 23.6 mg (0.08 mmol) of 1-(bromomethyl)pyrene (available from TRC) for 1-(chloromethyl)naphthalene. Monomer XIIa, where X is Br, is obtained as a solid.

Monomer XIIa, when $R_1$ and $R_2$ and $R_3$ are all methyl ($CH_3$), $R_6$ and $R_7$ are both H, $R_9$ is NH, a is 3 and X is Cl; is a quaternary ammonium salt of DMAPMA and 1-(chloromethyl)pyrene, which is synthesized using the same procedure as for Monomer I, except substituting 20.1 mg (0.08 mmol) of 1-(chloromethyl)pyrene (Beilstein 5 IV 2475) for 1-(chloromethyl)naphthalene. Monomer XIIa, where X is Cl, is obtained as a solid.

Monomer Example XIIb

Monomer XIIb, when $R_1$ and $R_2$ and $R_3$ are all methyl ($CH_3$), $R_6$ and $R_7$ are both H, $R_9$ is NH, a is 3 and X is Br; is a quaternary ammonium salt of DMAPMA and 2-(bromomethyl)pyrene. Monomer XIIb is synthesized using the same procedure as for Monomer I, except substituting 23.6 mg (0.08 mmol) of 2-(bromomethyl)pyrene (S. Akiyama, K. Nakasuji, and M. Nakagawa, *Bull. Chem. Soc. Jpn.*, 44, 1971, 2231–2236) for 1-(chloromethyl)naphthalene. Monomer XIIb, where X is Br, is obtained as a solid.

Monomer XIIb, when $R_1$ and $R_2$ and $R_3$ are all methyl ($CH_3$), $R_6$ and $R_7$ are both H, $R_9$ is NH, a is 3 and X is Br; is a quaternary ammonium salt of DMAPMA and 2-(chloromethyl)pyrene. Monomer XIIb is synthesized using the same procedure as for Monomer I, except substituting 20.1 mg (0.08 mmol) of 2-(chloromethyl)pyrene (Beilstein 5 IV 2476) for 1-(chloromethyl)naphthalene. Monomer XIIb, where X is Cl, is obtained as a solid.

Monomer Example XII

Monomer XIIc, where $R_1$ and $R_2$ and $R_3$ are all methyl ($CH_3$), $R_6$ and $R_7$ are both H, $R_9$ is NH, a is 3 and X is Br;

is a quaternary ammonium salt of DMAPMA and 4-(bromomethyl)pyrene. Monomer XIIc is synthesized using the same procedure as for Monomer I, except substituting 23.6 mg (0.08 mmol) of 4-(bromomethyl)pyrene (M. Konieczny, R. G. Harvey, *J. Org. Chem.*, 44(13), 1979, 2158–2160) for 1-(chloromethyl)naphthalene. Monomer XIIc, where X is Br, is obtained as a solid.

Monomer XIIc, where $R_1$ and $R_2$ and $R_3$ are all methyl ($CH_3$), $R_6$ and $R_7$ are both H, $R_9$ is NH, a is 3 and X is Cl; is a quaternary ammonium salt of DMAPMA and 4-(chloromethyl)pyrene, which is synthesized using the same procedure as for Monomer I, except substituting 20.1 mg (0.08 mmol) of 4-(chloromethyl)pyrene (Beilstein 5 IV 2477) for 1-(chloromethyl)naphthalene. Monomer XIIc, where X is Cl, is obtained as a solid.

Monomer Example XIII

Monomer XIII, where $R_1$ and $R_2$ and $R_3$ are all methyl ($CH_3$), $R_6$ and $R_7$ are both H, $R_9$ is NH, a is 3 and X is Cl; is a quaternary ammonium salt of DMAPMA and (5- and 6)-(((4-chloromethyl)benzoyl)amino)tetramethylrhodamine (5- and 6-mixed isomers). Monomer XIII is synthesized using the same procedure as for Monomer I, except substituting 44.3 mg (0.08 mmol) of (5- and 6 (sold as a mixture of these two isomers))-(((4-chloromethyl)benzoyl)amnino)tetramethylrhodamine (with the 5- and 6-position of attachment labeled on the structure), CellTracker™ Orange CMTMR, available from MOLECULAR PROBES, for 1-(chloromethyl)naphthalene. Monomer XIII is obtained as a solid.

Polymer Example Ia

Polymer Ia (emulsion), a fluorescent 70/30 mole percent AcAm/DMAEA·MCQ emulsion polymer with TAG Ia is synthesized by following this procedure:

An aqueous monomer phase solution is made by stirring together 0.0221 g (0.052 mmol) of the DMAPMA-1-(chloromethyl)naphthalene quaternary ammonium salt (Monomer Ia), 12.6 g of a 49.6% aqueous solution of acrylamide, 0.45 g of adipic acid, 1.35 g of NaCl, 9.06 g of a 80.3%, aqueous solution of DMAEA·MCQ, 7.84 g of water, and 0.18 g of a 5% aqueous solution of EDTA·4Na$^+$. The components are stirred until in solution.

An oil phase is prepared by heating a mixture of 11.7 g of paraffinic oil (Escaid-110, available from EXXON), 0.94 g of Tween®61 (POE (4) sorbitan monostearate, available from ICI), and 0.41 g of Span®80 (sorbitan monooleate, available from ICI) until the surfactants dissolved at about 55° C.

The oil-phase is charged into a 125 mL baffled reaction flask, and heated to 45° C. With vigorous stirring, the monomer phase is added dropwise over 2 minutes The resulting mixture is stirred for 65 minutes. To the water-in-oil emulsion is added 0.0149 g of AIBN (available from DUPONT) and 0.0014 g of AIVN (also available from DUPONT). The polymerization is carried out under a $N_2$ atmosphere for 3 hr and 50 minutes at 45° C., then 60° C. for one hour.

Polymer Ia (dispersion), a fluorescent 35 mole % water continuous dispersion polymer with Monomer Ia, is synthesized by combining 148 g of a 48.1% aqueous solution of acrylamnide, 130 g of a 80% aqueous solution of DMAEA·BCQ, 37 g of an 80% aqueous solution of DMAEA·MCQ, 15 g of glycerin, 50 g of a DADMAC/DMAEA·BCQ copolymer (20% aqueous solution), 0.30 g of ethylenediaminetetraacetic acid, tetrasodium salt, 156 g of ammonium sulfate, and 0.128 g of Monomer Ia (0.3 mmol). This mixture is charged to a 1.5 L reaction vessel equipped with a mixer, a thermocouple, a nitrogen purge tube and a water condenser, and heated to 48° C. with vigorous mixing. Upon reaching that temperature, 1.2 g of a 1% aqueous solution of V-50 (available from WAKO) is added and a nitrogen purge of the reactor contents is started. An additional 2.8 g of a 1% aqueous solution of V-50 is added after two hours. The mixture is polymerized for a total of six hours under these conditions, cooled to room temperature, and then 42 g of ammonium sulfate and 10 g of acetic acid is added to reduce the viscosity of the solution and to adjust the pH. The product of this reaction is a low viscosity fluid.

Polymer Ia (dry), a fluorescent acrylamide dry powder polymer with Monomer Ia, is synthesized in the following manner: In a 600 mL insulated reaction flask, 125.77 g of deionized water, 254 g of acrylamide solution (48.7%), 0.190 g of sodium hydroxide solution (50%), 0.43 g of acetic acid, and 0.080 g of Monomer Ia (0.2 mmol) are combined. To this solution is added 5.0 g of a 4% solution of V-501 (available from WAKO), 1.54 g of a 10% solution of Versenex®80 (available from DOW), 2.8 g of a 0.10% solution of sodium hypophosphite, 4.8 g of a 0.125% solution of ammonium persulfate, and 2.0 g of a 0.2% solution of ferrous ammonium sulfate. After this, the solution is purged with nitrogen, and within a few minutes the temperature of the solution will begin to rise. The temperature is allowed to increase adiabatically. After the temperature attains its maximum value, the reactor contents are allowed to cool to room temperature. The product of the polymerization is a rubbery gel which is shredded, dried, and ground to a fine powder.

Polymer Ia (solution), a partially neutralized acrylic acid solution polymer with Monomer Ia, is synthesized in the following manner: To a 1.5 L reaction flask equipped with an agitator, a thermocouple, a nitrogen,purge tube and a reflux condenser is added 64 g of deionized water, 450 g of acrylic acid, 22.5 g of sodium hydroxide,(50% solution) and 0.26 g of Monomer Ia (0.6 mmol). This mixture is heated to 70° C. and purged with nitrogen with vigorous mixing. Eight grams of ammonium persulfate is dissolved in 23 g of deionized water, and, separately, 79 g of sodium bisulfite is dissolved in 197 g of deionized water. The ammonium persulfate solution is added to the reaction mixture at the rate of 12 mL/hour, and the sodium bisulfite solution is added to the reaction mixture at the rate of 102 mL/hour. After 3.5 hours, 155 g of deionized water is added and the reaction mixture is cooled to room temperature. The product of the polymerization is a clear solution.

Polymer Example Ib

Polymer Ib (emulsion), a fluorescent 70/30 mole percent AcAm/DMAEA·MCQ emulsion polymer with TAG Ib is obtained using the same procedure as for Polymer Ia (emulsion), except 0.0187 g of Monomer Ib (0.052 mmol) is substituted for Monomer Ia.

Polymer Ib (dispersion), a fluorescent 35 mole % water continuous dispersion polymer with TAG Ib, is synthesized according to the procedure provided for Polymer Ia (dispersion) except that 0.108 g of Monomer Ib (0.300 mmol) is substituted for Monomer Ia (0.300 mmol).

Polymer Ib (dry), a fluorescent acrylamide, dry powder polymer with TAG Ib, is synthesized according to the procedure provided for Polymer Ia (dry), except that 0.072 g of Monomer Ib (0.200 mmol) is substituted for Monomer Ia (0.200 mmol).

Polymer Ib (solution), a partially neutralized acrylic acid solution polymer with TAG Ib, is synthesized according to the procedure provided for Polymer Ia (solution), except that 0.216 g of Monomer Ib (0.600 mmol) is substituted for Monomer Ia (0.6 mmol).

Polymer Example II

Polymer II (emulsion), a fluorescent 70/30 mole percent AcAm/DMAEA·MCQ emulsion polymer with TAG II is obtained using the same procedure as for Polymer Ia (emulsion), except 0.0179 g of Monomer II (0.052 mmol) is substituted for Monomer Ia.

Polymer II (dispersion), a fluorescent 35 mole % water continuous dispersion polymer with TAG II, is synthesized according to the procedure provided for Polymer Ia (dispersion) except that 0.104 g of Monomer II (0.300 mmol) is substituted for Monomer Ia (0.300 mmol).

Polymer II (dry), a fluorescent acrylamide dry powder polymer with TAG II, is synthesized according to the procedure provided for Polymer Ia (dry), except that 0.070 g of Monomer II (0.200 mmol) is substituted for Monomer Ia (0.200 mmol).

Polymer II (solution), a partially neutralized acrylic acid solution polymer with TAG II, is synthesized according to the procedure provided for Polymer Ia (solution), except that 0.208 g of Monomer II (0.600 mmol) is substituted for Monomer Ia (0.600 mmol).

Polymer Example III

Polymer III (emulsion), a fluorescent 70/30 mole percent AcAm/DMAEA·MCQ emulsion polymer with TAG III is obtained using the same procedure as for Polymer Ia (emulsion), except 0.0228 g of Monomer III (0.052 mmol) is substituted for Monomer Ia.

Polymer III (dispersion), a fluorescent 35 mole % water continuous dispersion polymer with TAG III, is synthesized according to the procedure provided for Polymer Ia (dispersion) except that 0.132 g of Monomer III (0.300 mmol) is substituted for Monomer Ia (0.300 mmol).

Polymer III (dry), a fluorescent acrylamide dry powder polymer with TAG III, is synthesized according to the procedure provided for Polymer Ia (dry), except that 0.088 g of Monomer III (0.200 mmol) is substituted for Monomer Ia (0.200 mmol).

Polymer III (solution), a partially neutralized acrylic acid solution polymer with TAG III, is synthesized according to the procedure provided for Polymer Ia (solution), except that 0.265 g of Monomer III (0.600 mmol) is substituted for Monomer Ia (0.600 mmol).

Polymer Example IV

Polymer IV (emulsion), a fluorescent 70/30 mole percent AcAm/DMAEA·MCQ emulsion polymer with TAG IV is obtained using the same procedure as for Polymer Ia (emulsion), except 0.0180 g of Monomer IV (0.052 mmol) is substituted for Monomer Ia.

Polymer IV (dispersion), a fluorescent 35 mole % water continuous dispersion polymer with TAG IV, is synthesized according to the procedure provided for Polymer Ia (dispersion) except that 0.104 g of Monomer IV (0.300 mmol) is substituted for Monomer Ia (0.300 mmol).

Polymer IV (dry), a fluorescent acrylamide dry powder polymer with TAG IV, is synthesized according to the procedure provided for Polymer Ia (dry), except that 0.070 g of Monomer IV (0.200 mol) is substituted for Monomer Ia (0.200 mmol).

Polymer IV (solution), a partially neutralized acrylic acid solution polymer with TAG IV, is synthesized according to the procedure provided for Polymer Ia (solution), except that 0.209 g of Monomer IV (0.600 mmol) is substituted for Monomer Ia (0.600 mmol).

Polymer Example V

Polymer V (emulsion), a fluorescent 70/30 mole percent AcAm/DMAEA·MCQ emulsion polymer with TAG V is obtained using the same procedure as for Polymer Ia (emulsion), except 0.5 g of a 0.96% solution of Monomer V in DMF (0.014 mmol) is substituted for 0.0221 g (0.052 mmol) of Monomer Ia.

Polymer V (dispersion), a fluorescent 35 mole % water continuous dispersion polymer with TAG V, is synthesized according to the procedure provided for Polymer Ia (dispersion) except that 10.5 g of a 0.96% solution in dimethylformamide of Monomer V (0.300 mmol) is substituted for Monomer Ia (0.300 mmol).

Polymer V (dry), a fluorescent acrylamide dry powder polymer with TAG V is synthesized according to the procedure provided for Polymer Ia (dry), except that 7.02 g of a 0.96% solution in dimethylformamide of Monomer V (0.200 mmol) is substituted for Monomer Ia (0.200 mmol).

Polymer V (solution), a partially neutralized acrylic acid solution polymer with TAG V, is synthesized according to the procedure provided for Polymer Ia (solution), except that 21.05 g of a 0.96% solution in dimethylformamide of Monomer V (0.600 mmol) is substituted for Monomer Ia (0.600 mmol).

Polymer Example VI

Polymer VI (emulsion), a fluorescent 70/30 mole percent AcAm/DMAEA·MCQ emulsion polymer with TAG VI is synthesized in the following manner. An aqueous monomer phase solution is made by stirring together 0.5 g of a 1.69% solution of the DMAPMA-5-bromomethylfluorescein quaternary salt in DMF (Monomer VI), 12.6 g of a 49.6% aqueous solution of acrylamide, 0.45 g of adipic acid, 1.35 g of NaCl, 9.06 g of a 80.3% aqueous solution of DMAEA·MCQ, 7.84 g of water, and 0.18 g of a 5% aqueous solution of EDTA·4Na$^+$. The components are stirred until in solution.

An oil phase is prepared by heating a mixture of 11.7 g of paraffinic oil (Escaid-110, available from EXXON), 0.94 g of Tween®61 (POE (4) sorbitan monostearate, available from ICI), and 0.41 g of Span®80 (sorbitan monooleate, available from ICI) until the surfactants dissolved (55° C.).

The oil-phase is charged into a 125 mL baffled reaction flask, and heated to 45° C. With vigorous stirring, the monomer phase is added dropwise over 2 minutes The resulting mixture is stirred for 65 minutes. To the water-in-oil emulsion is added 0.0149 g of AIBN (2,2'-azobis (isobutyronitrile), available from DUPONT) and 0.0014 g of AIVN (2,2'-azobis(2,4-dimethylvaleronitrile), available from DUPONT). The polymerization is carried out under a $N_2$ atmosphere for 3 hours and 45 minutes at 45° C., then 60° C. for one hour. An RSV of 16.7 dl/g (1M $NaNO_3$, 450 ppm, 30° C.) is measured for an aqueous solution of the resulting polymer.

Incorporation of the fluorescent TAG into the high molecular weight fractions of the polymer is verified chromatographically, using a 20 cm×7.8 mm ID column packed in-house with Waters Accell Plus QMA packing. A mobile phase containing 1% acetic acid, 0.10 M sodium sulfate and 0.01 M tetrabutylammonium hydrogen sulfate is used to separate tagged high molecular weight polymer from low molecular weight polymer and residual fluorescent monomer, if present. A waters 410 refractive index detector and a Shimadzu RF-530 fluorescence detector (EX/EM 438/518) are used simultaneously to quantitate incorporation and determine fluorescence relative to untagged controls.

Polymer VI (dispersion), a fluorescent 35 mole % water continuous dispersion polymer with TAG VI, is synthesized according to the procedure provided for Polymer Ia (dispersion) except that 10.6 g of a 1.68% solution in dimethylformamide of Monomer VI (0.300 mmol) is substituted for Monomer Ia (0.300 mmol).

Polymer VI (dry), a fluorescent acrylamide dry powder polymer with TAG VI, is synthesized according to the procedure provided for Polymer Ia (dry), except that 7.06 g of a 1.68% solution in dimethylformamide of Monomer VI (0.200 mmol) is substituted for Monomer Ia (0.200 mmol).

Polymer VI (solution), a partially neutralized acrylic acid solution polymer with TAG VI, is synthesized according to the procedure provided for Polymer Ia (solution), except that 21.20 g of a 1.68% solution in dimethylformamide of Monomer VI (0.600 mmol) is substituted for Monomer Ia (0.600 mmol).

Polymer Example VII

Polymer VII (emulsion), a fluorescent 70/30 mole percent AcAm/DMAEA·MCQ emulsion polymer with TAG VII is synthesized according to the procedure for Polymer Ia (emulsion) except 0.025 g (0.052 mmol) of the DMAPMA-3-bromomethyl-6,7-dimethoxy-1-methyl-2(1H)-quinoxazolinone quaternary salt (Monomer VII), is used in place of Monomer Ia. An RSV of 12.1 dl/g (1M NaNO$_3$, 450 ppm, 30° C.) is measured for a solution of the resulting polymer. TAG incorporation is confirmed using the dual detector LC technique (EX/EM 383/474 nm) described for Polymer Example VI.

Polymer VII (dispersion), a fluorescent 35 mole % water continuous dispersion polymer with TAG VII, is synthesized according to the procedure provided for Polymer Ia (dispersion) except that 0.145 g of Monomer VII (0.3 mmol) is substituted for Monomer Ia (0.300 mmol).

Polymer VII (dry), a fluorescent acrylamide dry powder polymer with TAG VII, is synthesized according to the procedure provided for Polymer Ia (dry), except that 0.097 g of Monomer VII (0.200 mmol) is substituted for Monomer Ia (0.200 mmol).

Polymer VII (solution), a partially neutralized acrylic acid solution polymer with TAG VII, is synthesized according to the procedure provided for Polymer Ia (solution), except that 0.290 g of Monomer VII (0.600 mmol) is substituted for Monomer Ia (0.600 mmol).

Polymer Example VIIIa

Polymer VIIIa (emulsion), a fluorescent 70/30 mole percent AcAm/DMAEA·MCQ emulsion polymer with Monomer VIIIa is obtained using the same procedure as for Polymer Ia, except 0.5 g of a 1.70% solution of Monomer VIIIa in DMF (0.014 mmol) is substituted for 0.0221 g (0.052 mmol) of Monomer Ia.

Polymer VIIIa (dispersion), a fluorescent 35 mole % water continuous dispersion polymer with TAG VIIIa, is synthesized according to the procedure provided for Polymer Ia (dispersion) except that 10.54 g of a 1.70% solution in dimethylformamide of Monomer VIIIa (0.300 mmol) is substituted for Monomer Ia (0.300 mmol).

Polymer VIIIa (dry), a fluorescent acrylamide dry powder polymer with TAG VIIIa, is synthesized according to the procedure provided for Polymer Ia (dry), except that 7.03 g of a 1.70% solution in dimethylformamide of Monomer VIIIa (0.200 mmol) is substituted for Monomer Ia (0.200 mmol).

Polymer VIIIa (solution), a partially neutralized acrylic acid solution polymer with TAG VIIIa, is synthesized according to the procedure provided for Polymer Ia (solution), except that 21.09 g of a 1.70% solution in dimethylformamide of Monomer VIIIa (0.600 mmol) is substituted for Monomer Ia (0.600 mmol).

Polymer Example VIIIb

Polymer VIIIb (emulsion), a fluorescent 70/30 mole percent AcAm/DMAEA·MCQ emulsion polymer with Monomer VIIIb is obtained using the same procedure as for Polymer Ia, except 0.5 g of a 1.99% solution of Monomer VIIIb in DMF (0.014 mmol) is substituted for 0.0221 g (0.052 mmol) of Monomer Ia.

Polymer VIIIb (dispersion), a fluorescent 35 mole % water continuous dispersion polymer with TAG VIIIb, is synthesized according to the procedure provided for Polymer Ia (dispersion) except that 10.57 g of a 1.99% solution in dimethylformamide of Monomer VIIIb (0.300 mmol) is substituted for Monomer Ia (0.300 mmol).

Polymer VIIIb (dry), a fluorescent acrylamide dry powder polymer with TAG VIIIb, is synthesized according to the procedure provided for Polymer Ia (dry), except that 7.05 g of a 1.99% solution in dimethylformamide of Monomer VIIIb (0.200 mmol) is substituted for Monomer Ia (0.200 mmol).

Polymer VIIIb (solution), a partially neutralized acrylic acid solution polymer with TAG VIIIb, is synthesized according to the procedure provided for Polymer Ia (solution), except that 21.16 g of a 1.99% solution in dimethylformamide of Monomer VIIIb (0.600 mmol) is substituted for Monomer Ia (0.600 mmol).

Polymer Example IX

Polymer IX (emulsion when X is Cl), a fluorescent 70/30 mole percent AcAm/DMAEA·MCQ emulsion polymer with Monomer IX (X is Cl) is obtained using the same procedure as for Polymer Ia (emulsion), except 0.5 g of a 1.32% solution of Monomer IX (where X is Cl) in DMF (0.014 mmol) is substituted for 0.0221 g (0.052 mmol) of Monomer Ia.

Polymer IX (emulsion when X is Br), a fluorescent 70/30 mole percent AcAm/DMAEA·MCQ emulsion polymer with Monomer IX (X is Br) is obtained using the same procedure as for Polymer Ia (emulsion), except 0.5 g of a 1.45% solution of Monomer IX (X is Br) in DMF (0.014 mmol) is substituted for 0.0221 g (0.052 mmol) of Monomer Ia.

Polymer IX (dispersion, where X is Cl), a fluorescent 35 mole % water continuous dispersion polymer with TAG IX, is synthesized according to the procedure provided for Polymer Ia (dispersion) except that 10.61 g of a 1.32% solution in dimethylformamide of Monomer IX (where X is Cl, 0.300 mmol) is substituted for Monomer Ia (0.300 mmol).

Polymer IX (dispersion, where X is Br), a fluorescent 35 mole % water continuous dispersion polymer with TAG IX, is synthesized according to the procedure provided for Polymer Ia (dispersion) except that 10.61 g of a 1.45% solution in dimethylformamide of Monomer IX (where X is Br, 0.300 mmol) is substituted for Monomer Ia (0.300 mmol).

Polymer IX (dry, where X is Cl), a fluorescent acrylamide dry powder polymer with TAG IX, is synthesized according to the procedure provided for Polymer Ia (dry), except that 7.07 g of a 1.32% solution in dimethylformamide of Monomer IX (where X is Cl, 0.200 mmol) is substituted for Monomer Ia (0.200 mmol).

Polymer IX (dry, where X is Br), a fluorescent acrylamide dry powder polymer with TAG IX, is synthesized according to the procedure provided for Polymer Ia (dry), except that 7.07 g of a 1.45% solution in dimethylformamide of Monomer IX (where X is Br, 0.200 mmol) is substituted for Monomer Ia (0.200 mmol).

Polymer IX (solution, where X is Cl), a partially neutralized acrylic acid solution polymer with TAG IX, is synthesized according to the procedure provided for Polymer Ia (solution), except that 21.22 g of a 1.32% solution in dimethylformamide of Monomer IX (where X is Cl, 0.600 mmol) is substituted for Monomer Ia (0.600 mmol).

Polymer IX (solution, where X is Br), a partially neutralized acrylic acid solution polymer with TAG IX, is synthesized according to the procedure provided for Polymer Ia (solution), except that 21.22 g of a 1.45% solution in dimethylformamide of Monomer IX (where X is Br, 0.600 mmol) is substituted for Monomer Ia (0.600 mmol).

Polymer Example X

Polymer X (emulsion), a fluorescent 70/30 mole percent AcAm/DMAEA·MCQ emulsion polymer with Monomer X is obtained using the same procedure as for Polymer Ia (emulsion), except 0.5 g of a 1.54% solution of Monomer X in DMF (0.014 mmol) is substituted for 0.0221 g (0.052 mmol) of Monomer Ia.

Polymer X (dispersion), a fluorescent 35 mole % water continuous dispersion polymer with TAG X, is synthesized according to the procedure provided for Polymer Ia (dispersion) except that 10.58 g of a 1.54% solution in dimethylformamide of Monomer X (0.300 mmol) is substituted for Monomer Ia (0.300 mmol).

Polymer X (dry), a fluorescent acrylamide dry powder polymer with TAG X, is synthesized according to the procedure provided for Polymer Ia (dry), except that 7.05 g of a 1.54% solution in dimethylformamide of Monomer X (0.200 mmol) is substituted for Monomer Ia (0.200 mmol).

Polymer X (solution), a partially neutralized acrylic acid solution polymer with TAG X, is synthesized according to the procedure provided for Polymer Ia (solution), except that 21.16 g of a 1.54% solution in dimethylformamide of Monomer X (0.600 mmol) is substituted for Monomer Ia (0.600 mmol).

Polymer Example XI

Polymer XI (emulsion), a fluorescent 70/30 mole percent AcAm/DMAEA·MCQ emulsion polymer with Monomer XI is obtained using the same procedure as for Polymer Ia (emulsion), except 0.5 g of a 1.25% solution of Monomer XI in DMF (0.014 mmol) is substituted for 0.0221 g (0.0552 mmol) of Monomer Ia.

Polymer XI (dispersion), a fluorescent 35 mole % water continuous dispersion polymer with TAG XI, is synthesized according to the procedure provided for Polymer Ia (dispersion) except that 10.59 g of a 1.25% solution in dimethylformamide of Monomer XI (0.300 mmol) is substituted for Monomer Ia (0.300 mmol).

Polymer XI (dry), a fluorescent acrylamide dry powder polymer with TAG XI, is synthesized according to the procedure provided for Polymer Ia (dry), except that 7.06 g of a 1.25% solution in dimethylformamide of Monomer XI (0.200 mmol) is substituted for Monomer Ia (0.200 mmol).

Polymer XI (solution), a partially neutralized acrylic acid solution polymer with TAG XI, is synthesized according to the procedure provided for Polymer Ia (solution), except that 21.19 g of a 1.25% solution in dimethylformamide of Monomer XI (0.600 mmol) is substituted for Monomer Ia (0.600 mmol).

Polymer Example XIIa

Polymer XIIa (emulsion, when X is Cl), a fluorescent 70/30 mole percent AcAm/DMAEA·MCQ emulsion polymer with Monomer XIIa (X is Cl) is obtained using the same procedure as for Polymer Ia (emulsion), except 0.0218 g of Monomer XIIa (X is Cl, 0.052 mmol) is substituted for 0.0221 g (0.052 mmol) of Monomer Ia.

Polymer XIIa (emulsion, when X is Br), a fluorescent 70/30 mole percent AcAm/DMAEA·MCQ emulsion polymer with Monomer XIIa (X is Br) is obtained using the same procedure as for Polymer Ia (emulsion), except 0.0241 g of Monomer XIIa (X is Br, 0.052 mmol) is substituted for 0.0221 g (0.052 mmol) of Monomer Ia.

Polymer XIIa (dispersion, when X is Cl) is a fluorescent 35 mole % water continuous dispersion polymer with TAG XIIa, is synthesized according to the procedure provided for Polymer Ia (dispersion) except that 0.126 g of Monomer XIIa (X is Cl, 0.300 mmol) is substituted for Monomer Ia (0.300 mmol).

Polymer XIIa (dispersion, when X is Br) is a fluorescent 35 mole % water continuous dispersion polymer with TAG XIIa, is synthesized according to the procedure provided for Polymer Ia (dispersion) except that 0.140 g of Monomer XIIa (X is Br, 0.300 mmol) is substituted for Monomer Ia (0.300 mmol).

Polymer XIIa (dry, when X is Cl), a fluorescent acrylamide dry powder polymer with TAG XIIa, is synthesized according to the procedure provided for Polymer Ia (dry), except that 0.084 g of Monomer XIIa (X is Cl, 0.200 mmol) is substituted for Monomer Ia (0.200 mmol).

Polymer XIIa (dry, when X is Br), a fluorescent acrylamide dry powder polymer with TAG XIIa, is synthesized according to the procedure provided for Polymer Ia (dry), except that 0.093 g of Monomer XIIa (X is Br, 0.200 mmol) is substituted for Monomer Ia (0.200 mmol).

Polymer XIIa (solution, when X is Cl), a partially neutralized acrylic acid solution polymer with TAG XIIa, is synthesized according to the procedure provided for Polymer Ia (solution), except that 0.252 g of Monomer XIIa, (X is Cl, 0.600 mmol) is substituted for Monomer Ia (0.600 mmol).

Polymer XIIa (solution, when X is Br), a partially neutralized acrylic acid solution polymer with TAG XIIa, is synthesized according to the procedure provided for Polymer Ia (solution), except that 0.279 g of Monomer XIIa, (X is Br, 0.600 mmol) is substituted for Monomer Ia (0.600 mmol).

Polymer Example XIIb

Polymer XIIb (emulsion, when X is Cl), a fluorescent 70/30 mole percent AcAm/DMAEA·MCQ emulsion polymer with Monomer XIIb (X is Cl) is obtained using the same procedure as for Polymer Ia (emulsion), except 0.0218 g of Monomer XIIb (X is Cl 0.052 mmol) is substituted for 0.0221 g (0.052 mmol) of Monomer Ia.

Polymer XIIb (emulsion, when X is Br), a fluorescent 70/30 mole percent AcAm/DMAEA·MCQ emulsion polymer with Monomer XIIb (X is Br) is obtained using the same procedure as for Polymer Ia (emulsion), except 0.0241 g of Monomer XIIb (X is Br, 0.052 mmol) is substituted for 0.0221 g (0.052 mmol) of Monomer Ia.

Polymer XIIb (dispersion, when X is Cl), a fluorescent 35 mole % water continuous dispersion polymer with TAG XIIb is synthesized according to the procedure provided for Polymer Ia (dispersion) except that 0.126 g of Monomer XIIb (X is Cl, 0.300 mmol) is substituted for Monomer Ia (0.300 mmol).

Polymer XIIb (dispersion, when X is Br), a fluorescent 35 mole % water continuous dispersion polymer with TAG XIIb is synthesized according to the procedure provided for Polymer Ia (dispersion) except that 0.140 g of Monomer XIIb (X is Br, 0.300 mmol) is substituted for Monomer Ia (0.300 mmol).

Polymer XIIb (dry, when X is Cl), a fluorescent acrylamide dry powder polymer with TAG XIIa, is synthesized according to the procedure provided for Polymer Ia (dry), except that 0.084 g of TAG XIIb, (X is Cl, 0.200 mmol) is substituted for Monomer Ia (0.200 mmol).

Polymer XIIb (dry, when X is Br), a fluorescent acrylamide dry powder polymer with TAG XIIa, is synthesized according to the procedure provided for Polymer Ia (dry), except that 0.093 g of TAG XIIb, (X is Br, 0.200 mmol) is substituted for Monomer Ia (0.200 mmol).

Polymer XIIb (solution, when X is Cl), a partially neutralized acrylic acid solution polymer with TAG XIIb, is synthesized according to the procedure provided for Polymer Ia (solution), except that 0.252 g of Monomer XIIb, (X is Cl, 0.600 mmol) is substituted for Monomer Ia (0.600 mmol).

Polymer XIIb (solution, when X is Br), a partially neutralized acrylic acid solution polymer with TAG XIIb, is synthesized according to the procedure provided for Polymer Ia (solution), except that 0.279 g of Monomer XIIb, (X is Br, 0.600 mmol) is substituted for Monomer Ia (0.600 mmol).

Polymer Example XIIC

Polymer XIIc (emulsion, when X is Cl), a fluorescent 70/30 mole percent AcAm/DMAEA·MCQ emulsion polymer with Monomer XIIc (X is Cl) is obtained using the same procedure as for Polymer Ia (emulsion), except 0.0218 g of Monomer XIIc (X is Cl, 0.052 mmol) is substituted for 0.0221 g (0.052 mmol) of Monomer Ia.

Polymer XIIc (emulsion, when X is Br), a fluorescent 70/30 mole percent AcAm/DMAEA·MCQ emulsion polymer with Monomer XIIc (X is Br) is obtained using the same procedure as for Polymer Ia (emulsion), except 0.0241 g of Monomer XIIc (X is Br, 0.052 mmol) is substituted for 0.0221 g (0.052 mmol) of Monomer Ia.

Polymer XIIc (dispersion, when X is Cl), a fluorescent 35 mole % water continuous dispersion polymer with TAG XIIc, is synthesized according to the procedure provided for Polymer Ia (dispersion) except that 0.126 g of Monomer XIIc (X is Cl, 0.300 mmol) is substituted for Monomer Ia (0.300 mmol).

Polymer XIIc (dispersion, when X is Br), a fluorescent 35 mole % water continuous dispersion polymer with TAG XIIc, is synthesized according to the procedure provided for Polymer Ia (dispersion) except that 0.140 g of Monomer XIIc (X is Br, 0.300 mmol) is substituted for Monomer Ia. (0.300 mmol).

Polymer XIIc (dry, when X is Cl), a fluorescent acrylamide dry powder polymer with TAG XIIc is synthesized according to the procedure provided for Polymer Ia (dry), except that 0.084 g of Monomer XIIc (X is Cl, 0.200 mmol) is substituted for Monomer Ia (0.200 mmol).

Polymer XIIc (dry, when X is Br), a fluorescent acrylamide dry powder polymer with TAG XIIc is synthesized according to the procedure provided for Polymer Ia (dry), except that 0.093 g of Monomer XIIc (0.200 mmol) is substituted for Monomer Ia (0.200 mmol).

Polymer XIIc (solution, when X is Cl), a partially neutralized acrylic acid solution polymer with TAG XIIc, is synthesized according to the procedure provided for Polymer Ia (solution), except that 0.252 g of Monomer XIIc, (X is Cl, 0.600 mmol) is substituted for Monomer Ia (0.600 mmol).

Polymer XIIc (solution, when X is Br), a partially neutralized acrylic acid solution polymer with TAG XIIc, is synthesized according to the procedure provided for Polymer Ia (solution), except that 0.279 g of Monomer XIIc, (X is Br, 0.600 mmol) is substituted for Monomer Ia (0.600 mmol).

Polymer Example XIII

Polymer XIII (emulsion), a fluorescent 70/30 mole percent AcAm/DMAEA·MCQ emulsion polymer with Monomer XIII is obtained using the same procedure as for Polymer Ia (emulsion), except 0.0375 g of Monomer XIII is substituted for 0.0221 g (0.052 mmol) of Monomer Ia.

Polymer XIII (dispersion), a fluorescent 35 mole % water continuous dispersion polymer with TAG XIII, is synthesized according to the procedure provided for Polymer Ia (dispersion) except that 0.217 g of Monomer XIII (0.300 mmol) is substituted for Monomer Ia (0.300 mmol).

Polymer XIII (dry), a fluorescent acrylamide dry powder polymer with TAG XIII, is synthesized according to the procedure provided for Polymer Ia (dry), except that 0.145 g of Monomer XIII (0.200 mmol) is substituted for Monomer Ia (0.200 mmol).

Polymer XIII (solution), a partially neutralized acrylic acid solution polymer with TAG XIII, is synthesized according to the procedure provided for Polymer Ia (solution), except that 0.436 g of Monomer XIII (0.600 mmol) is substituted for Monomer Ia (0.600 mmol).

Method Example I

The utility of tagged water-in-oil emulsion polymers in monitoring polymer location and in dosage control is demonstrated utilizing polymers VI (emulsion) and VII (emulsion) to dewater sludge from a midwestern municipal wastewater treatment facility.

A free drainage test is performed to evaluate the dewatering performance of aqueous polymer solutions prepared from tagged polymers. A one (1) weight percent solution of the tagged polymer product to be tested is prepared. 200 mL of the sludge is placed in a 500 mL graduated cylinder. Different amounts of the tagged polymer solution are next added to the sludge. Finally, water is added to the cylinder, to adjust the volume of the mixture to 225 mL. The graduated cylinder is then inverted to flocculate the particles in the sludge, then the contents of the graduated cylinder are gravity filtered through a fabric filter and the effluent drainage for a given time (usually 10 seconds) is recorded. A more effective flocculant is indicated by a higher volume of effluent which is able to pass through the filter in the given time. The effluent collected is retained for fluorescence analysis.

For this experiment, the fluorescence is analyzed directly using a Hitachi F-4500 fluorescence spectrophotometer. An increase in measured fluorescence is observed over the background when the optimal polymer dosage is reached. The results are illustrated in Table I and Table II. Calibration curves for these polymers developed on a fluorescence spectrophotometer in the sludge matrix are generated to allow a conversion from relative fluorescence (over background) to ppm polymer, if desired. This experiment shows that the polymers of the instant claimed invention can be used to determine when the optimal amount of treatment flocculant has been added.

TABLE I

Polymer VI detection after Municipal Sludge Dewatering

| Polymer[1] Dosage (mL) | Drainage[2] (mL) | Fluorescence Intensity[3] |
|---|---|---|
| 0* | — | 3630* |
| 2 | 70 | 3704 |
| 3 | 130 | 3816 |
| 5 | 150 | 4738 |
| 7 | 140 | 6338 |
| 9 | 144 | 7987 |

[1]A 30 mole % cationic (70/30 mole ratio acrylamide/DMAEA.MCQ tagged with 0.012 mole percent of Monomer VI, synthesized according to the method of Polymer Example VI (emulsion).
[2]The level of filtrate collected after 10 seconds, two cylinder inversions.
[3]EX/EM = 438/518 nm.
*Sludge blank. Fluorescence of supernatant after centrifuging sludge sample at 2000 rpm for 30 minutes.

TABLE II

Polymer VII detection after Municipal Sludge Dewatering

| Polymer[1] Dosage (mL) | Drainage[2] (mL) | Fluorescence Intensity[3] |
|---|---|---|
| 0 | — | 999* |
| 2 | 72 | 1029 |
| 3 | 116 | 1095 |
| 5 | 144 | 1389 |
| 7 | 142 | 1694 |
| 9 | 142 | 1862 |

[1]A 30 mole % cationic (70/30 mole ratio acrylamide/DMAEA.MCQ tagged with 0.041 mole percent of Monomer VII, synthesized according to the method of Polymer Example VII (emulsion)).
[2]The level of filtrate collected after 10 seconds.
[3]EX/EM = 383/474 nm.
*Sludge blank. Fluorescence of supernatant after centrifuging sludge sample at 2000 rpm for 30 minutes.

In Table I and in Table II, an increase in fluorescence over background as a function of polymer dosage is observed. Above a dosage of 5 mL of polymer, a large increase in fluorescent intensity is evident. Since the marked increase in measured fluorescence occurs at the polymer dosage which is optimal for drainage (after which further increases in polymer dosage produce little or no increases in drainage volume), the use of the tagged polymers in this situation represent an indirect method for correlating polymer dosage to optimum drainage. The ability to exploit this effect has practical implications for optimizing various sludge dewatering processes and programs by providing a means to correlate polymer dosage to maximum drainage. There are also obvious economic benefits associated with the ability to determine when an overdose of the polymer is occurring, that is to say; that more polymer is being applied than is required for efficient drainage. Such a determination is made by monitoring the relative changes in fluorescence in the effluent for the present example. cl Method Example II The utility of fluorescently tagged polymers for the correlation of optimal polymer dosage with turbidity reduction in pulp and paper applications is demonstrated for paper furnish retention uses with a synthetic alkaline fine paper furnish (80% hardwood kraft/softwood kraft (60/40), 20% calcium carbonate) using polymers VI (emulsion) and VII (emulsion).

A standard Britt jar experiment is used to evaluate the retention activity of aqueous polymer solutions prepared from tagged emulsion polymers in a paper furnish. The Britt Jar Test uses a Britt CF Dynamic Drainage Jar developed by K. W. Britt of New York University, which generally consists of an upper chamber of about 1-liter capacity and a bottom drainage chamber, the chambers being separated by a support screen and a drainage screen. Below the drainage chamber is a flexible tube extending downward equipped with a clamp for closure. The upper chamber is provided with a 2-inch, 3-blade propeller to create controlled shear conditions in the upper chamber. The appropriate concentration of aqueous polymer solution is prepared to give a convenient dosage, such as 1 ml=0.5 lb/ton. The Britt jar test conditions for a typical experiment are given as follows:

| Furnish: | Synthetic Alkaline Furnish (500 mL) |
|---|---|
| Consistency: | 0.5% |
| Jar: | Standard three vaned |
| Screen: | 60 m |
| Drainage rate: | 70–75 ml/30 sec |
| RPM: | 1250 |
| Polymer Concentration: | 0.0625 wt % (actives) |

The test is conducted by following the sequence below:

| Time (seconds) | Action |
|---|---|
| 0 | Commence shear via mixing at 1250 rpm; add synthetic furnish. |
| 10 | Add starch (10 lb/t). |
| 20 | Add flocculant to be tested. |
| 30 | Open the tube clamp to commence drainage. |
| 60 | Stop draining and measure turbidity of filtrate. |

The starch used is Solvitose N, a cationic potato starch, commercially available from Nalco Chemical Company. The material drained from the Britt Jar (the "filtrate") is collected and diluted five fold with water to provide a turbidity which is conveniently measured. The turbidity of such diluted filtrate is then determined in Nephelometric or Formazine Turbidity Units (NTU or FTU). The turbidity of such a filtrate is inversely proportional to the papermaking retention performance; the lower the turbidity value (or higher the turbidity reduction), the higher is the retention of filler and/or fines. Therefore the lower the turbidity, the more efficient the flocculent. The turbidity values are measured at 450 nm using a Hach DR-2000 Turbidimeter.

The fluorescence of the filtrate is measured directly using a Hitachi F-4500 fluorescence spectrophotometer. In Britt jar retention experiments with synthetic alkaline furnish, with both polymers VI (emulsion) and VII (emulsion), prepared according to the procedure of Polymer Example VI and Polymer Example VII, an increase in fluorescence over background as a function of polymer dosage was observed. These data are shown in Table III and Table IV.

TABLE III

Polymer VI Detection in Standard Alkaline Furnish

| Polymer[1] Dosage[2] | % Turbidity Reduction | Fluorescence Intensity[3] |
|---|---|---|
| 0* | 32.9 | 183 |
| 0.5 | 48.6 | 235 |
| 1.0 | 61.3 | 144 |
| 2.0 | 71.3 | 174 |
| 4.0 | 78.7 | 459 |

[1]A 30 mole % cationic (70/30 mole ratio acrylamide/DMAEA.MCQ tagged with 0.012 mole percent of Monomer VI, synthesized according to the method of Polymer Example VI (emulsion)).
[2]Pound active per ton solids.
[3]EX/EM = 438/518 nm.
*10 lb/ton starch, no polymer.

TABLE IV

Polymer VII Detection in Standard Alkaline Furnish

| Polymer[1] Dosage[2] | % Turbidity Reduction | Fluorescence Intensity[3] |
|---|---|---|
| 0* | 32.9 | 223 |
| 1.0 | 59.4 | 299 |
| 2.0 | 66.6 | 261 |
| 4.0 | 67.9 | 441 |
| 6.0 | 65.5 | 700 |

[1]A 30 mole % cationic (70/30 mole ratio acrylamide/DMAEA.MCQ tagged with 0.041 mole percent of Monomer VII, synthesized according to the method of Polymer Example VII (emulsion)).
[2]Pound active per ton solids.
[3]EX/EM = 383/474 nm.
*10 lb/ton starch, no polymer.

Beyond a polymer dosage of 2 pounds per ton (on a polymer actives basis), a marked increase in fluorescence of the filtrate is observed, corresponding to a decrease in the rate of turbidity reduction. Therefore, by using the tagged polymers to monitor changes in the fluorescence of the filtrate as a function of polymer dosage, the ability to optimize the polymer dosage for a specific parameter of interest, in this case, the reduction of filtrate turbidity is obtained.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A fluorescent monomer selected from the group consisting of:

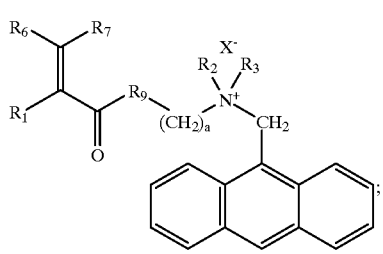

MONOMER III

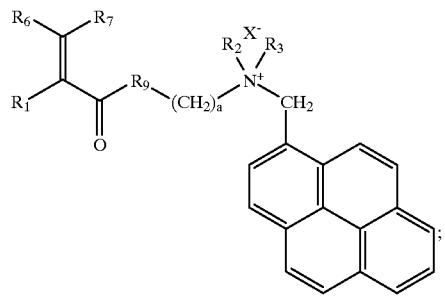

MONOMER XIIa

MONOMER XIIb

MONOMER XIIc wherein a is an integer of from 1 to 10, $R_1$ is selected from the group consisting of hydrogen and methyl groups, $R_2$ and $R_3$ are methyl groups, $R_9$ is selected from the group consisting of NE and O; $R_6$ is either hydrogen or methyl; and $R_7$ is either hydrogen or methyl; and X— is selected from the group consisting of chloride, iodide, sulfate, acetate, benzoate, phosphate and bromide.

* * * * *